Figure 2A:
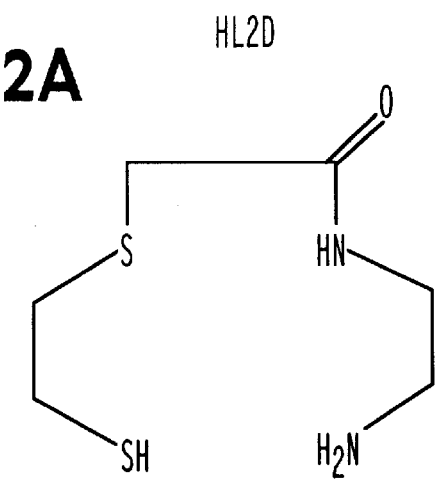
Figure 2B:
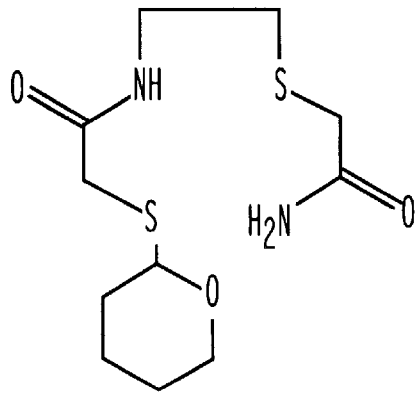
Figure 2C:
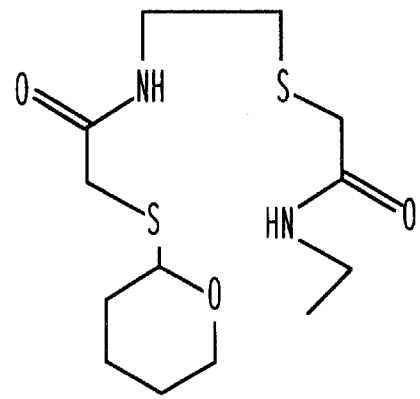
Figure 3A:
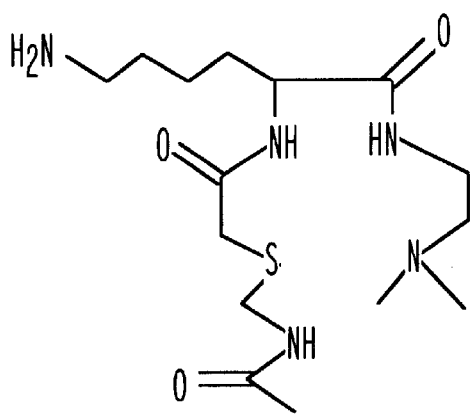
Figure 3B:
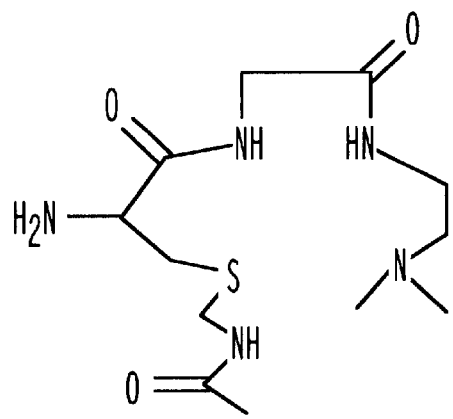
Figure 3C:
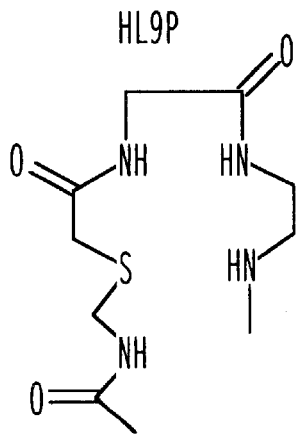
Figure 3D:
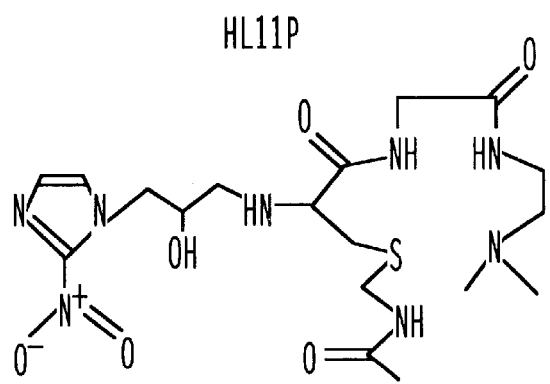
Figure 3E:
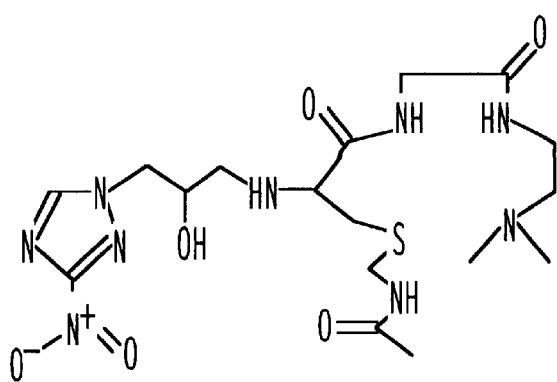
Figure 3F:
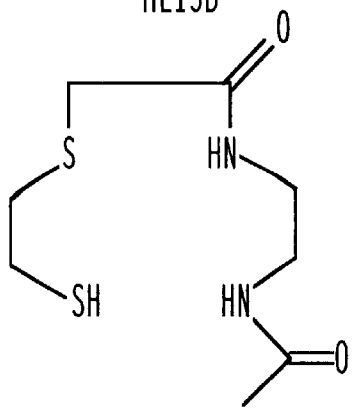
Figure 4A:
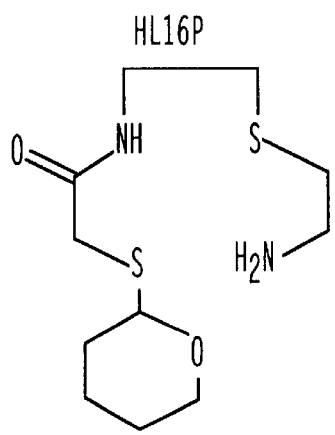
Figure 4B:
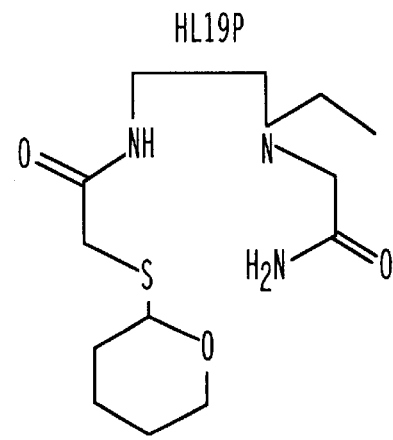
Figure 4C:
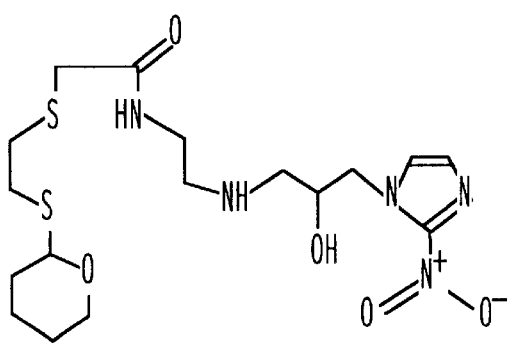
Figure 4D:
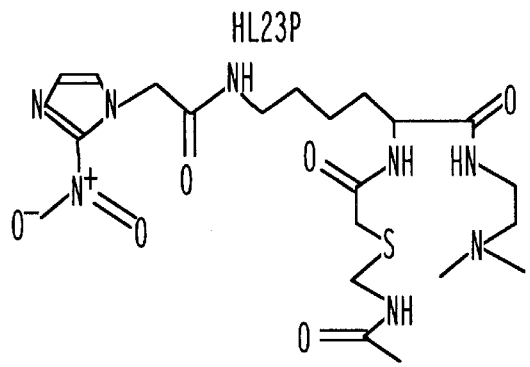
Figure 4E:
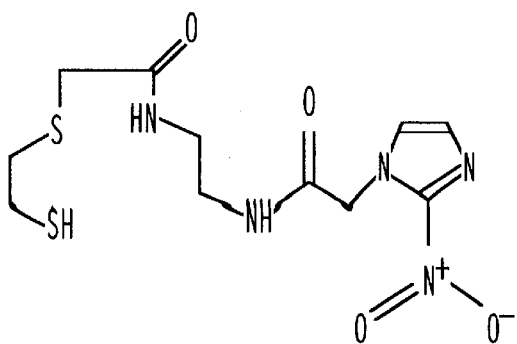
Figure 4F:
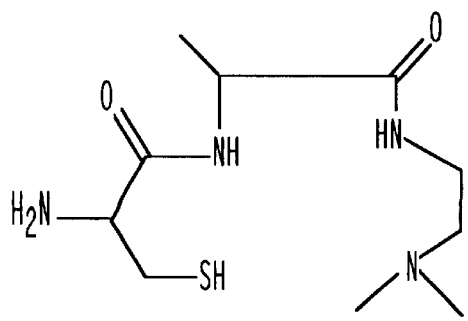
Figure 5A:
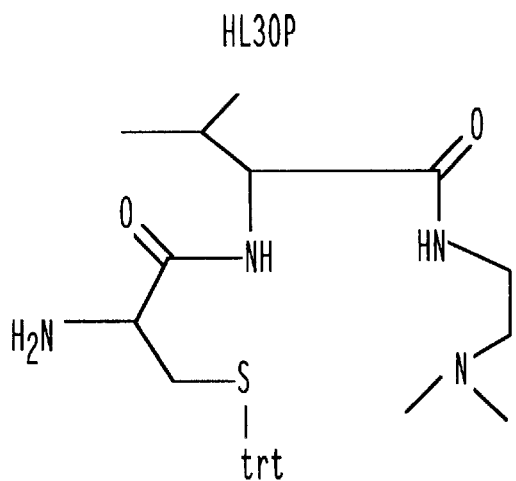
Figure 5B:
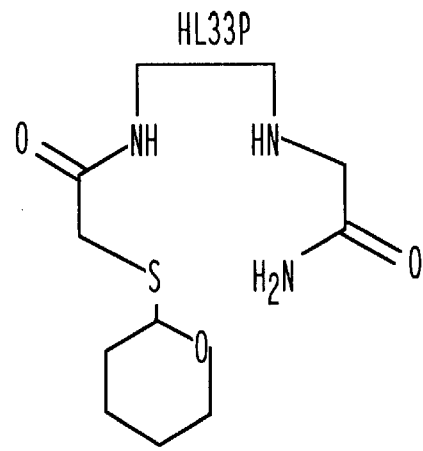
Figure 5C:
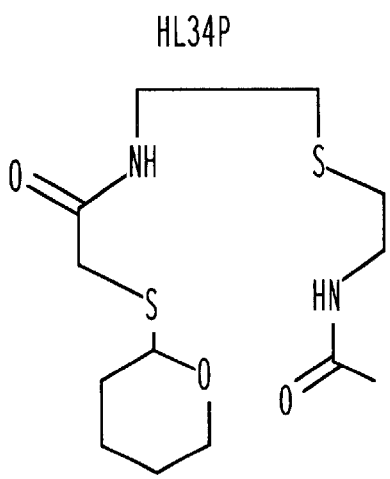
Figure 5D:
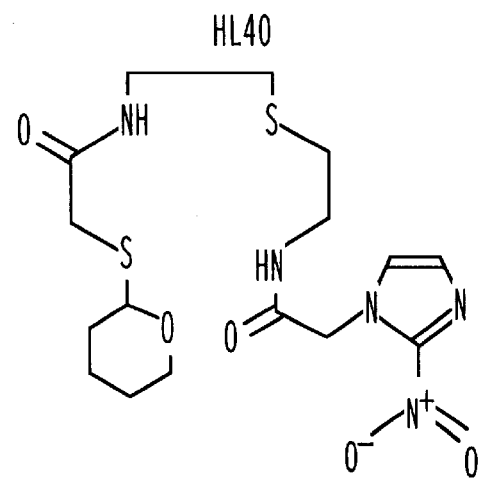
Figure 5E:
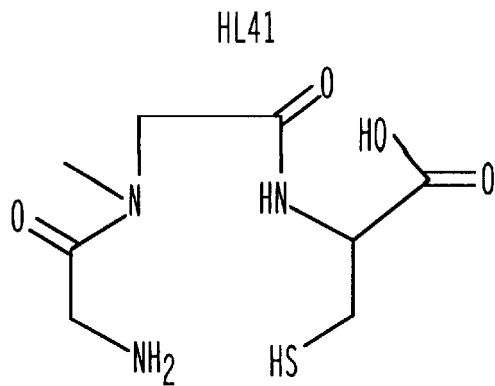
Figure 5F:
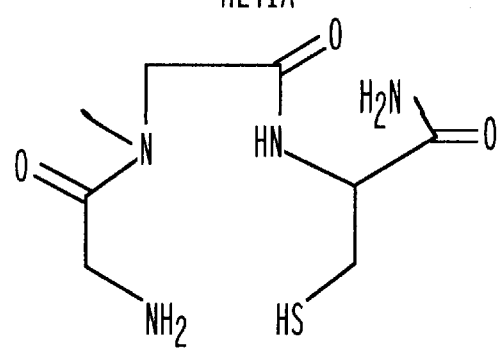
Figure 6A:
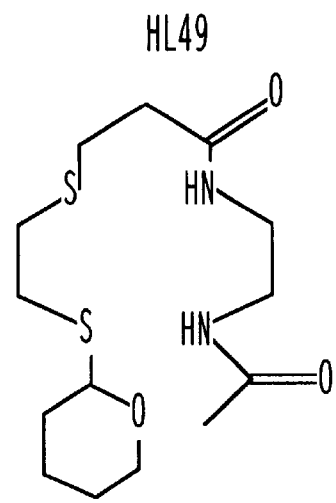
Figure 6B:
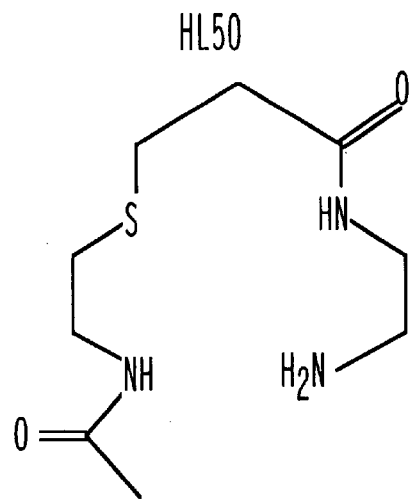
Figure 6C:
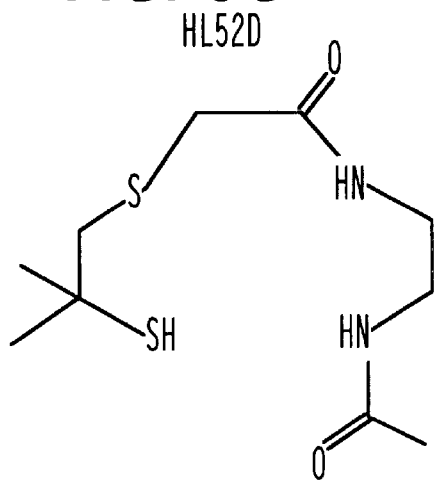
Figure 6D:
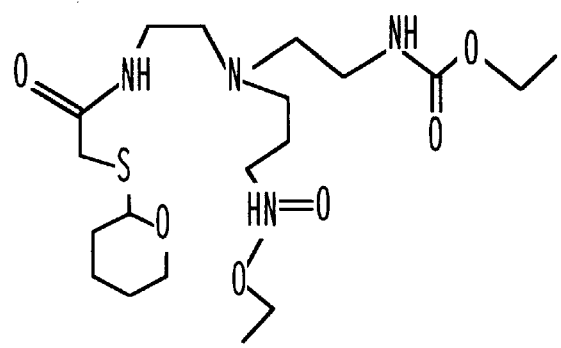
Figure 6E:
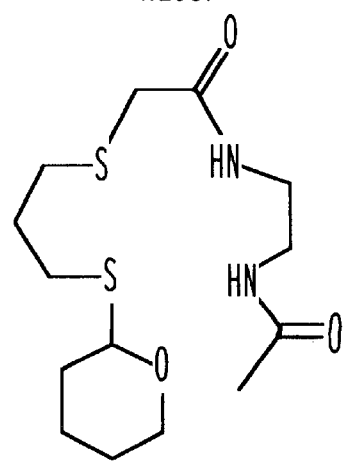
Figure 7A:
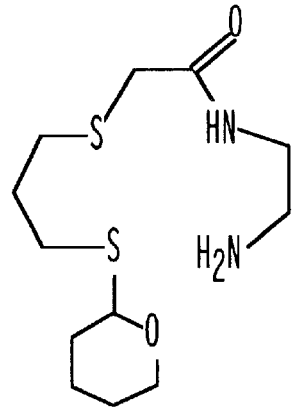
Figure 7B:
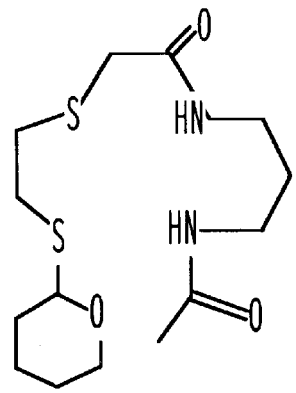
Figure 7C:
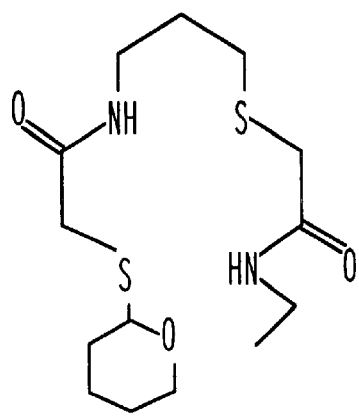
Figure 7D:
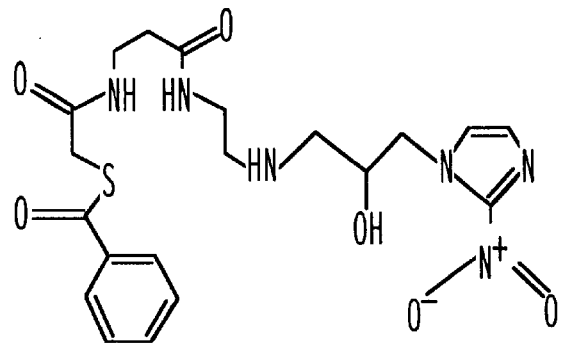
Figure 7E:
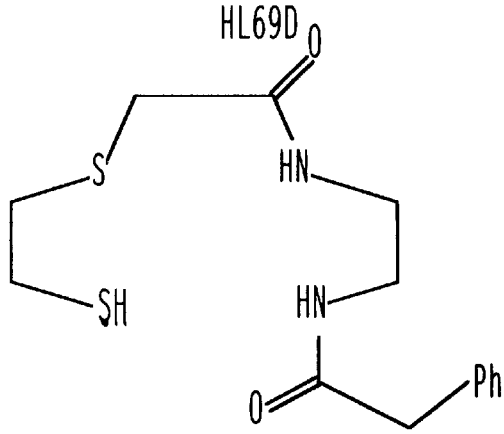
Figure 7F:
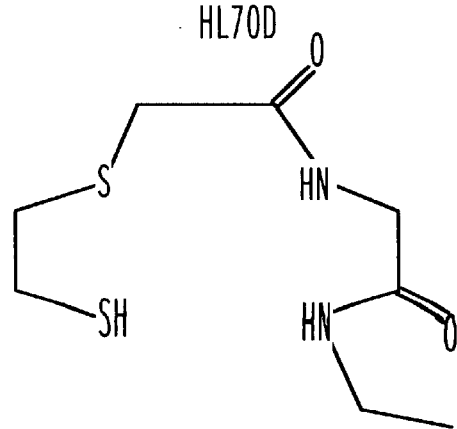
Figure 8A:
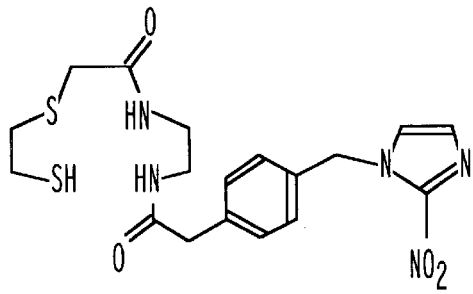
Figure 8B:
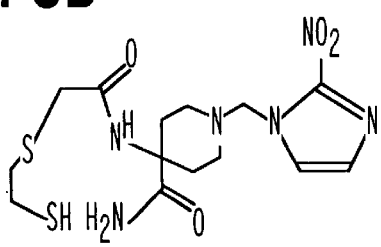
Figure 8C:
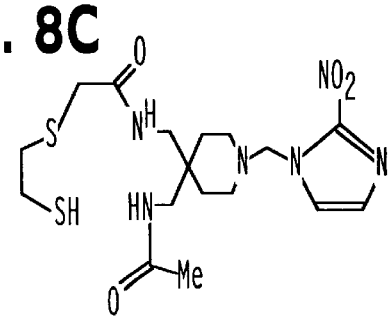
Figure 8D:
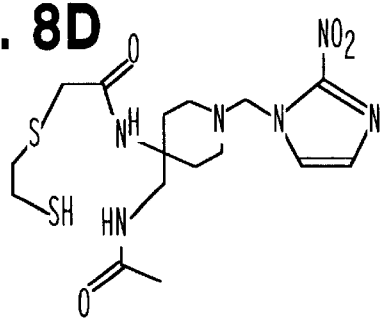
Figure 8E:
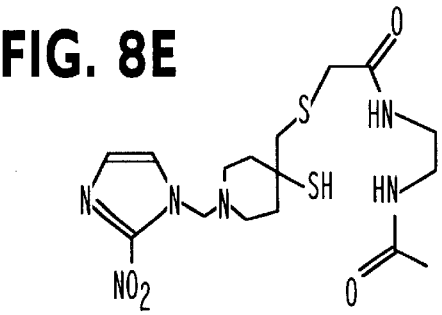
Figure 8F:
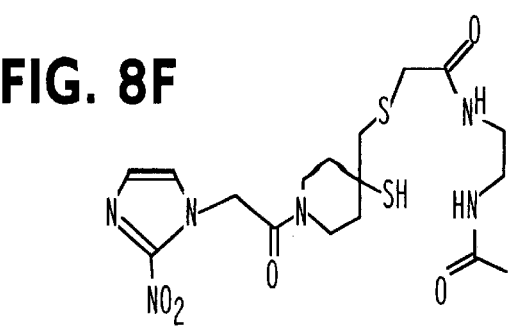
Figure 9A:
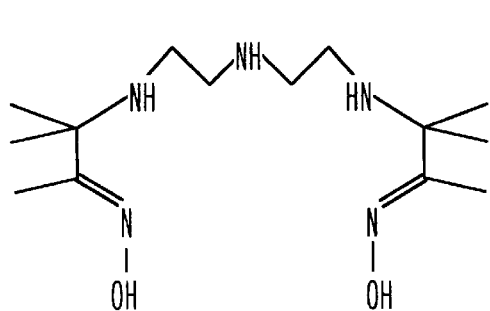
Figure 9B:
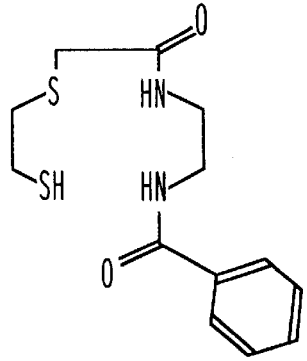
Figure 9C:
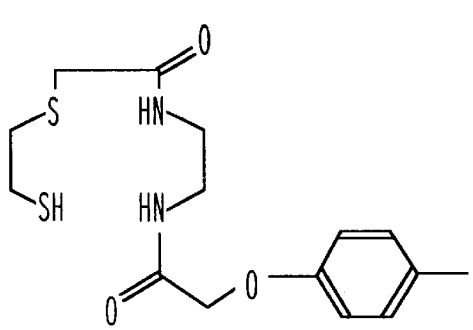
Figure 9D:
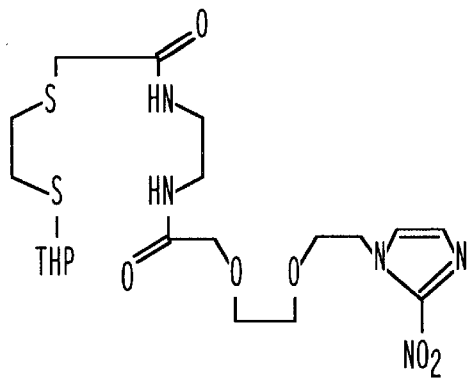
Figure 9E:
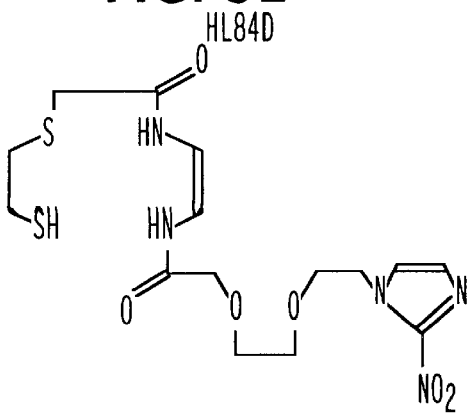
Figure 9F:
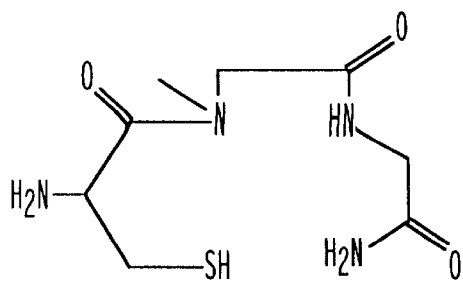
Figure 10A:
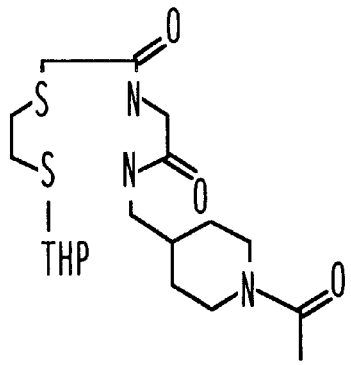
Figure 10B:
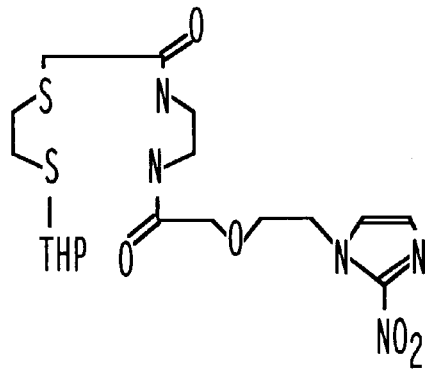
Figure 10C:
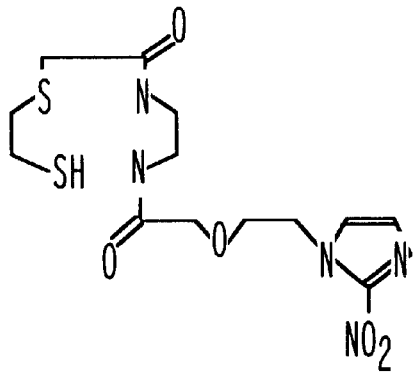
Figure 10D:
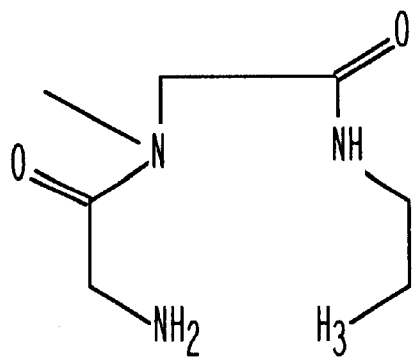

United States Patent [19]

Archer et al.

[11] Patent Number: 6,004,531

[45] Date of Patent: Dec. 21, 1999

[54] METAL CHELATING COMPOUNDS HAVING AN SNNN DONOR SET

[75] Inventors: Colin Mill Archer, Chesham; Gary Robert Bower, Aylesbury; Harjit Kaur Gill, Chesham; Anthony Leonard Mark Riley, Marlow; Anthony Eamon Storey, Amersham; Lewis Reuben Canning, Chesham; David Vaughan Griffiths, Colchester, all of United Kingdom

[73] Assignee: Nycomed Amersham plc, United Kingdom

[21] Appl. No.: 08/917,476

[22] Filed: Aug. 26, 1997

Related U.S. Application Data

[62] Division of application No. 08/888,398, Jul. 7, 1997, which is a continuation of application No. 08/356,383, filed as application No. PCT/GB94/00693, Mar. 31, 1994, abandoned.

[30] Foreign Application Priority Data

Apr. 2, 1993 [EP] European Pat. Off. ............ 93302634

[51] Int. Cl.[6] .............................. A61K 51/04; C07F 5/00; C07D 233/28; C07C 327/00
[52] U.S. Cl. ........................ 424/1.65; 424/1.69; 534/10; 534/14; 534/16; 548/327.5; 558/254
[58] Field of Search .................................. 534/10, 14, 16; 424/1.65, 1.69, 1.53, 9.36, 9.364, 9.365; 549/149, 496; 548/517, 548, 327.5; 558/254; 560/110, 251

[56] References Cited

U.S. PATENT DOCUMENTS

| | | |
|---|---|---|
| 5,091,514 | 2/1992 | Fritzberg et al. . |
| 5,112,953 | 5/1992 | Gustavson et al. . |
| 5,187,264 | 2/1993 | Verbruggen . |
| 5,387,692 | 2/1995 | Riley et al. .......................... 548/313.7 |
| 5,688,485 | 11/1997 | Harris ..................................... 424/1.65 |

FOREIGN PATENT DOCUMENTS

| | | |
|---|---|---|
| 0 542 216 | 5/1993 | European Pat. Off. . |
| WO90/05733 | 5/1990 | WIPO . |
| WO91/16076 | 10/1991 | WIPO . |

*Primary Examiner*—S. Mark Clardy
*Assistant Examiner*—Michael G. Hartley
*Attorney, Agent, or Firm*—Wenderoth, Lind & Ponack, L.L.P.

[57] ABSTRACT

Ligands for radiopharmaceutical use are capable of chelating radiometal species and of being bound to biological targeting molecules. The ligands have formula (a) and (b), where A, A'=—SZ or Y, B=O or S, Y=(c), Z=H or a thiol protecting group, m=2 or 3, n=2 or 3, q=0 or 1, R=H or unsubstituted or substituted hydrocarbon and pharmaceutically acceptable salts, provided that at least one $CR_2$ group represents CO and forms, together with an adjacent N atom, a —CONR— amide group.

9 Claims, 10 Drawing Sheets

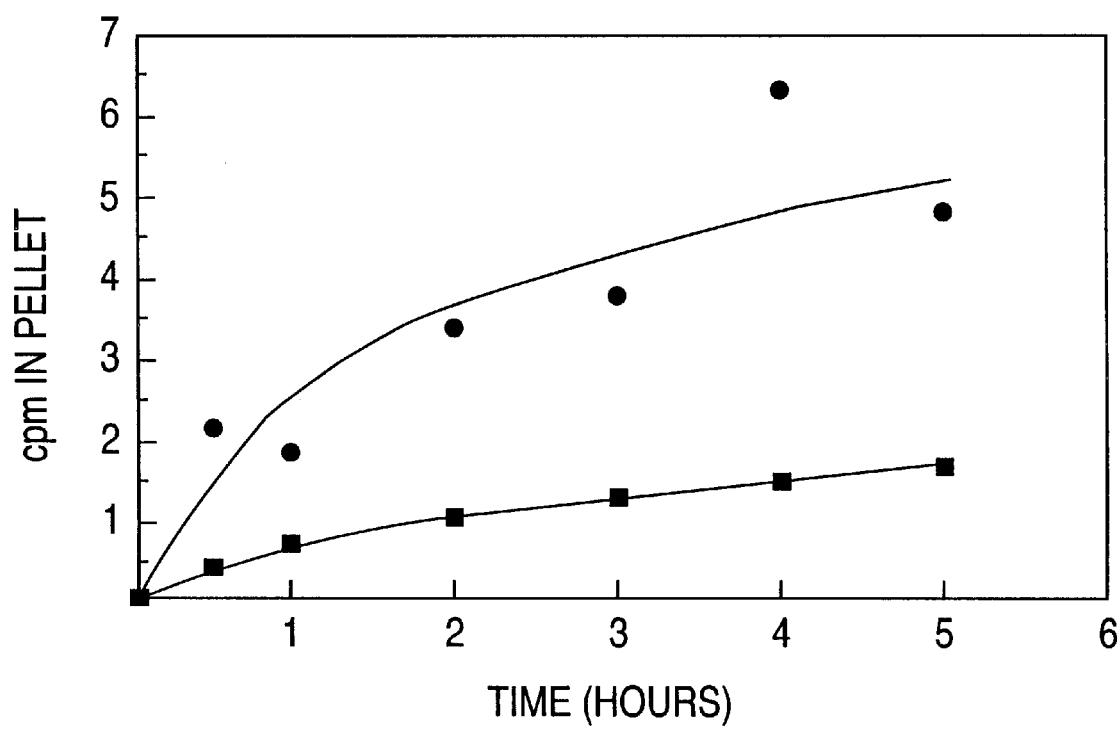

HL7P

HL8P

HL9P

HL11P

HL12P

HL15D

HL16P

HL19P

HL22P

HL23P

HL24D

HL29D

HL30P

HL33P

HL34P

HL40

HL41

HL41A

HL49

HL50

HL52D

HL53

HL58P

HL59P

HL60P

HL61P

HL64

HL69D

HL70D

HL72D 1 (FROM HL70)

3 (FROM HL60)

2 (FROM HL15)

4 (FROM HL15)

5 (FROM HL15)

HL81

MOL. WT.: 301.44

HL82D

MOL. WT.: 298.43

HL83D

MOL. WT.: 342.48

HL84P

MOL. WT.: 519.64

HL84D

MOL. WT.: 435.52

HL85S

MOL. WT.: 248.31

HL86P

MOL. WT.: 431.6

HL87P

MOL. WT.: 475.6

HL87D

MOL. WT.: 391.5

HL88

MOL. WT.: 205.3

METAL CHELATING COMPOUNDS HAVING AN SNNN DONOR SET

This is a divisional application of Ser. No. 08/888,398, filed Jul. 7, 1997, which is a continuation of now abandoned Ser. No. 08/356,383, filed Dec. 2, 1994, which is a 371 of PCT/GB94/00693, filed Mar. 31, 1994.

This invention concerns ligands which are intended mainly for radiopharmaceutical use. The ligands are capable of chelating radiometal species. The ligands are adapted to be bound, or are already bound, to biological targeting molecules.

The conventional approach to radionuclide labelling of biological targeting molecules is to attach known radiometal complexes to the targeting molecule. Relatively little consideration, however, has been given to the impact which the radiometal complex may have on the biodistribution of the targeting molecule. Thus introduction of a complex which exhibits high plasma protein binding may significantly increase the blood levels of the complex. Similarly, attachment of a charged hydrophilic radiometal complex may adversely affect the cell membrane permeability of the targeting molecule. In both cases the biodistribution of the radiolabelled targeting molecule complex no longer corresponds to that of the unlabelled targeting molecule.

PRIOR ART DISCUSSION

1 Ligands

The ligands DADS[1] and MAG$_3$ (Fritzberg, U.S. Pat. No. 4,980,147) form technetium complexes which are

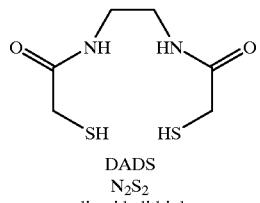

DADS
N$_2$S$_2$
diamidedithiol

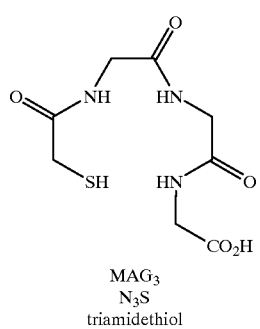

MAG$_3$
N$_3$S
triamidethiol hydrophilic anions and useful as kidney function agents. The diaminedithiol ligand BAT (Kung, EP 0,200,211 A1) forms a neutral lipophilic technetium

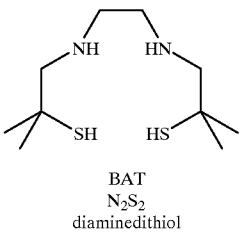

BAT
N$_2$S$_2$
diaminedithiol complex which can cross the blood-brain barrier.

Jones and Davison (U.S. Pat. No. 4,746,505) disclosed the S-functionalised N$_2$S$_2$ thioether ligand shown. It forms a neutral technetium complex which is unstable with respect to S-dealkylation regenerating the parent

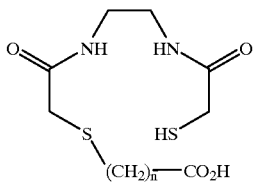

DADS complex[2].

The technetium complexes of monoaminemonoamide (MAMA) ligands have been

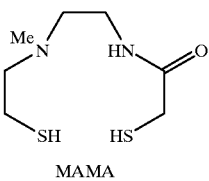

MAMA described[3]. The main thrust of the work was towards ligands with more favourable labelling kinetics than diamidethiols (such as DADS). U.S. Pat. No. 4,988,496 (Fritzberg) discloses that bifunctional MAMA derivatives are useful for antibody/protein labelling.

U.S. Pat. No. 4,925,650 claims the technetium complexes of N$_2$S$_2$ and N$_3$S ligands with pendant carboxyl groups as kidney function agents. The only ligand described is the diaminedithiol shown:

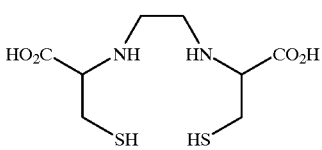

Brandau et al.[4] have described the renal imaging properties of a technetium complex of the carboxyl-substituted amine/amide/thioether/thiol ligand shown:

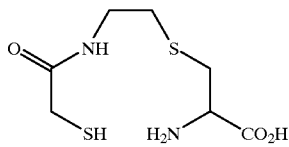

The nature of the technetium complex is not made clear in the abstract.

2 Chelate-Targeting Molecule Conjugates

There is a vast literature on the use of bifunctional chelating agents for the attachment of ligands to relatively high molecular weight biological targeting entities such as monoclonal antibodies (or their fragments) and proteins. Much less work has been done on coupling metal complexes to smaller targeting molecules (TM) such as peptides and receptor ligands.

U.S. Pat. No. 4,431,627 (Eckelman) covers ligands coupled to quinuclidinylbenzilates (QNB) as potential $^{99m}$Tc receptor imaging agents. QNB is a ligand for the muscarinic cholinergic receptor. Known ligands are specified, i.e. cyclam and dithiosemicarbazone (DTS-vide infra). No examples of chelate QNB conjugates or any new ligands are given.

U.S. Pat. No. 4,479,930 (Hnatowich) covers a method of attaching known chelating agents to the amine group of a biological targeting molecule (e.g. a polypeptide or antibody) for radiometal labelling. The cyclic anhydrides of the established aminocarboxylate ligands EDTA and DTPA are used.

U.S. Pat. No. 4,732,864 (DuPont) covers conjugates of biological targeting molecules (antibodies or their fragments, hormones, peptides, proteins or receptor ligands) with metallothionein or metallothionein fragments. Metallothionein is a polypeptide which binds metals via the sulphydryl moieties of its cysteine residues. The metal binding capability of metallothionein is described at Columns 3–5.

WO 91/17173 (Cytogen) claims conjugates of metal-binding metallothionein fragments with various polypeptides for radiopharmaceutical applications, including thrombus imaging.

GB 2225579 (Sandoz) claims chelates conjugated to a targeting polypeptide, somatostatin for tumour imaging. The ligands specified are the known compounds: BAT, DTS, PnAO, DADS, or aminocarboxylate ligands (e.g. EDTA, DTPA or TETA).

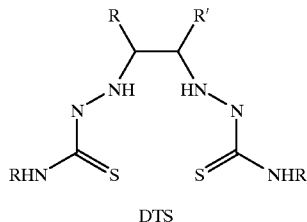

DTS

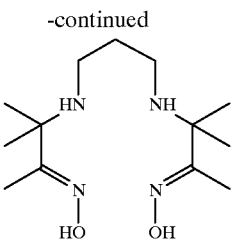

PnAO

EP 0,403,243 Al (Merck Frosst Canada) discloses chelate derivatives of the targeting polypeptide ANF (atrial natriuretic factor). Again, only known ligands are specified, e.g. DTPA, HBED and BAT.

WO 92/13572 (Diatech) claims the technetium binding tripeptide sequence Cys/aminoacid/Cys (a metallothionein fragment) linked to polypeptides for a variety of radiopharmaceutical applications.

EP 0,441,491 (Squibb) claims boronic acid adducts of $^{99m}$Tc dioxime complexes which are linked via an alkyl or alkenyl linker to a biochemically active group. The biochemically active group may be, e.g. a nitroimidazole (for hypoxia imaging), a steroid, or a muscarinic receptor ligand. The radiometal complex used is the previously known BATO system.

K E Linder et al.$^{(5)}$ described a nitroimidazole linked to PnAO for technetium complexation and hypoxia imaging.

The Invention

It is an object of this invention to provide a range of ligands and their respective radiometal complexes conjugated to biological targeting molecules, which complexes have either little or no effect or a beneficial effect, on the biodistribution properties of the targeting molecule.

In one aspect the invention provides ligands of the formula a)

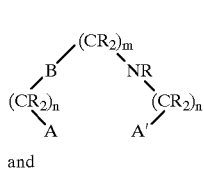

and b)

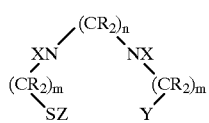

where

A, A'=—SZ or Y

B=O or S

Y=

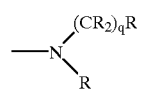

Z=H or a thiol protecting group m=2 or 3 n=2 or 3 q=0 or 1

R=same or different and is H, $C_1$–$C_{20}$ hydrocarbon which may be alkyl or one or more of alkenyl, alkoxy, alkoxyalkyl, primary secondary or tertiary amide, primary secondary or tertiary amine, carboxylic acid, hydroxyalkyl, aryl, or two R's of any $CR_2$ group and/or two or more adjacent $CR_2$ groups may be combined to form a $C_{3-6}$ cycloalkyl, aryl, heteroaryl, spiropiperidinyl or other saturated or unsaturated heterocyclic ring, or the two R groups of a $CR_2$ group adjacent a N atom may be combined to represent a —CONR— amide group,

X=R, and pharmaceutically acceptable salts of the ligands, provided that i) at least one $CR_2$ group represents CO and forms, together with an adjacent N atom, a —CONR— amide group, ii) at least one R may represent a targeting group or a protein reactive functionality, iii) when one or more of R is $C_{1-5}$ carboxyl, then at least one $CR_2$ group, that represents CO and forms, together with an adjacent N atom, a —CONR— amide group, is selected from $(CR_2)_m$ and $(CR_2)_q$, and iv) when each X is H, then only one or two $CR_2$ groups represents CO and forms, together with an adjacent N atom, a —CONR— amide group.

The thiol protecting group Z may be trityl, benzoyl, tetrahydropyran, benzyl, acetamidomethyl, or the corresponding disulphide dimer or others well known in the art.

The invention envisages that these ligand systems can be used to radiolabel biologically active species, especially small molecules (molecular weight less than a thousand) with minimal or beneficial effect on their biodistribution and activity. Thus in the compounds of the invention, at least one group R, and preferably one or two groups R, may comprise a targeting group and/or a protein reactive functionality. Examples of targeting groups are:

bioreductive molecules (e.g. 2-nitroimidazole)—for diagnosis/therapy of hypoxia and hypoxic tumours;

peptides—e.g. somatostatin analogues for cancer diagnosis and therapy, or cell adhesion peptides containing the RGD sequence for thrombus imaging;

receptor ligands—e.g. dopamine ligands for brain receptor imaging, steroids for estrogen receptor imaging;

enzyme inhibitors or substrates;

metabolic markers—glucose or fatty acids to track myocardial and/or brain metabolism, diacylglycerols;

proteins and antibodies—the cell permeation of the complexes can also be used to advantage in radioactive labelling of blood cells (leucocytes, red blood cells, platelets, lymphocytes) for in vivo diagnosis and therapy.

Protein reactive functionalities are well known and include for example isothiocyanate, haloacetamide, active ester, thioester, amino, mercapto, hydrazino, carboxyl, alkenyl or alkynyl, oxiranyl, aziridino, fluorinated phenoxycarbonyl, optionally substituted succinimidoxycarbonyl, aminophenyl, isothiocyanatophenyl, and others.

In these compounds, the bioreductive moiety may be any which has the ability to cause the agent to become trapped in hypoxic cells, for example those discussed by P. Mason in "Free Radicals in Biology", Academic Press, 1982, including quinones and aromatic nitro-compounds. Preferred are benzotriazine-di-n-oxides, triazoles, nitroacridines, nitrofurans, nitroimidazoles including particularly 2-nitroimidazole, and their substituted analogues such as misonidazole. Alkyl, acyl, chloro-, bromo-, hydroxyalkyl, alkoxyalkyl, aminoalkyl, and other substituents may improve the properties of these bioreductive molecules. Other references to bioreductive molecules include: J. H. Tocher et al., Free Rad. Res. Comms., Vol 10, Nos. 4–5, pp 295–302, 1990; Y. Nagao et al., Tetrahedron, Vol. 46, No. 9, pp 3211–3232, 1990; and W. A. Denny et al., J. Med. Chem., 1990, 33, 1288–1295.

In these compounds, a metal chelating moiety is joined to a targeting group by means of a linking group, which preferably comprises a chain from 1 to 12 atoms long, in which hetero atoms such as S, N and O are possible, as also are amide and ester linkages. The linking group should not be so charged or so polar as to prevent diffusion of a complex (of the compound with a radiometal) through cell walls. The linking group may comprise a rigid spacer group, such as one based on a piperidine ring or others known in the art. Rigid spacer groups may be particularly useful when the targeting group is a nitroimidazole.

Each of the ligands of formulae a) and b) contains four donor atoms selected from S, O and N which are capable of acting together to form a coordination complex with a radiometal. Preferably one or two of those four atoms are S, with the remaining two or three atoms being N. Preferably at least one of A and A' (in formula a)) is Y.

As noted above, one or two groups R may represent a targeting group or a protein reactive functionality. A group R that represents a targeting group or a peptide reactive functionality, together with any linking group present, is not subject to the $C_1$–$C_{20}$ size limitation and other features of the other R's. Elsewhere in the ligands, R is preferably hydrogen, primary amine, carboxylic acid, or C1 to C4 alkyl which may be substituted with primary amine or carboxylic acid.

It is an important feature of the invention that at least one $CR_2$ group represents CO and forms, together with an adjacent N atom, a —CONR— amide group. Preferably one, two or three, most usually one or two, $CR_2$ groups represents Co in this way. Preferably one or two of the resulting —CONR— amide groups is —CONR— amide.

In the ligands of this invention, there are generally present two or three or four potentially ionisable groups selected from —SH, —CONH—, —COOH and —NH—. The number of these potentially ionisable groups determines, in conjunction with the valency of the complexed radiometal ion, the electrical state, cationic or neutral or anionic, of the radiometal complex. In all the ligands discussed herein, the thiol protecting group Z is removed during radiometal labelling. Thus, protected thiol groups count for this purpose as —SH thiol groups. —NH— groups may be anionic or neutral depending on circumstances, with secondary amine groups —NH— having a greater tendency to lose a proton upon co-ordination than primary amine groups. Preferably the potentially ionisable groups are selected from —SH and —CONH—.

The ligands of this invention may be made by known chemical reactions from known starting materials. Preparative details are given in the experimental section below and in the reaction schemes 1 to 8.

The invention also includes radiometal complexes of the ligands described.

The term radiometal is used herein to describe the metal species which may be present in a variety of oxidation states, or even associated with O, OH, Cl, etc., depending on its chemistry. Preferred radiometals include $^{99m}$Tc, $^{186}$Re, $^{188}$Re, $^{67}$Cu and $^{107}$Ag. The radiometal complexes are readily made by allowing the mixed reagents to stand at room temperature. For example, technetium $^{99m}$ complexes may be made by mixing a solution of the metal chelating ligand with technetium generator eluate, in the presence of a reducing agent, and allowing the mixture to stand at ambient temperature for some minutes or hours. In some cases heating may be required.

Many of these radiometal complexes will be electrically neutral. For example it is expected (although this has not yet been demonstrated unequivocally) that radiometal complexes of technetium-99m will have the formula [$^{99m}Tc^V$-O L] where L is the ligand. When the ligand contains three anionic groups, the charge on these should balance out the +3 charge on the Tc-O group, resulting in an electrically neutral complex. Other radiometal complexes may be cationic, e.g. when the ligand contains two anionic groups; or anionic e.g. when the ligand contains four anionic groups.

Choice of a suitable complex type from a range of varying charge, size, lipophilicity etc., permits control over the degree of plasma protein binding, cell permeation ability, clearance route, etc., all important parameters in radiopharmaceutical design. Plasma protein binding is a significant factor in the development of a diagnostic imaging agent both in terms of free complex available for uptake in target tissue[6] and lack of pharmacokinetic interactions with other therapeutic agents[7]. Neutral complexes are preferred where the targeting molecule needs to cross cell membranes. In certain cases, coupling to certain radiometal complexes may have a beneficial effect on the biodistribution of the parent targeting molecule for imaging or radiotherapeutic purposes. This may be seen in improved concentration at the target (e.g. due to increased cell permeation) or increased background clearance with retention of targeting characteristics.

When a bioreductive moiety is present, the complexes of this invention are useful as hypoxia agents.

In vitro, the agent is capable of diffusing freely into oxic or hypoxic cells, but is preferentially trapped in hypoxic cells. In vivo where the agent is transported by the blood to hypoxic regions it diffuses through the cell walls. Once within the hypoxic cells it is a substrate for nitroreductases producing free radicals which, in the absence of $O_2$, become trapped, e.g. as a result of covalent bonding, within the cell. For these purposes, the agent has certain characteristics:

The agent as a whole is capable of diffusing into cells, for which purpose its partition coefficient is important. If the agent is too hydrophilic, it will not diffuse through cell walls. If it is too hydrophobic, it may be completely water-insoluble. The hydrophilic/lipophilic balance can quite readily be adjusted, e.g. by addition of hydrophilic or hydrophobic groups to the chelating moiety or to the linking group or to the bioreductive moiety, provided that the molecule should not be so charged or so polar as to prevent its diffusion through the cell walls.

Once in hypoxic cells, the agent is capable of being immobilised. For this purpose, the nitro or other bioreductive moiety should not be hindered by the chelating moiety.

The chelating moiety strongly binds the metal, and does not significantly release it in solution or in the bloodstream. Thus, the metal is introduced and becomes immobilised within the hypoxic cells.

Radiometal complexes of this invention are expected to be useful for tumour imaging or radiotherapy using, e.g. bioreductive targeting molecules for hypoxic tumours or polypeptides for other tumour types. The complexes can also be used for labelling receptor ligands (e.g. for brain dopamine receptor imaging) or metabolic markers such as fatty acids (R=$C_{6-20}$ carboxyl)

Reference is directed to the accompanying drawings, in which:

FIG. 1 is a graph showing the in vitro binding of 99m-Tc HL11P to V79 cells.

The remaining figures show various ligands according to the invention. The following ligands: HL11P; HL12P; HL22P; HL23P; HL24D; HL40; HL64; HL70; 1 (from HL7O); 2 (from HL15); 3 (from HL60); 4 (from HL15); 5 (from HL15); comprise a nitroimidazole targeting group joined by various linking groups to the chelating moiety. In the last five named, the linking groups comprise rigid spacer groups.

The following experimental section is divided into several parts:

The synthesis of various ligands is described in outline with the aid of reaction schemes 1 to 8 and spectral data for the ligands are given.

The radiolabelling of various ligands with 99m-pertechnetate, to give radiometal complexes according to the invention, is described.

Biological properties of these radiometal complexes, including plasma protein binding, red cell ghost uptake and hypoxic and oxic cell binding, are demonstrated.

The final section contains a more detailed description of the preparation and spectral properties of various ligands.

REFERENCES

1. A R Fritzberg et al. J.Nucl.Med., 22, 258 (1981).
2. A G Jones, A Davison et al. Inorg. Chem., 27, 2154 (1988).
3. A R Fritzberg et al. Nucl.Med.Biol., 19, 889 (1992).
4. W Brandau et al. J.Nucl.Med., 33, 919 (1992).
5. K E Linder et al. ibid. 33, P865 and P919 (1992).
6. E Deutsch et al. Nucl.Med.Biol., 16 191 (1989).
7. J H Lin et al. Clin. Pharmacokinetics, 12, 402 (1987).
8. Beaman et al. Antimicrobial Agents and Chemotherapy 7, 520 (1968).
9. J A Sophianopoulos et al. Arch. Biochem Biophys. 187 132 (1978),
10. O Jeghers et al. Eur. J. Nucl. Med., 17, 101 (1990).
11. T L Steck and J A Kant, Meth. Enzymol., 31 172 (1974).
12. R Messmann et al. Blood, 75 1711 (1990).

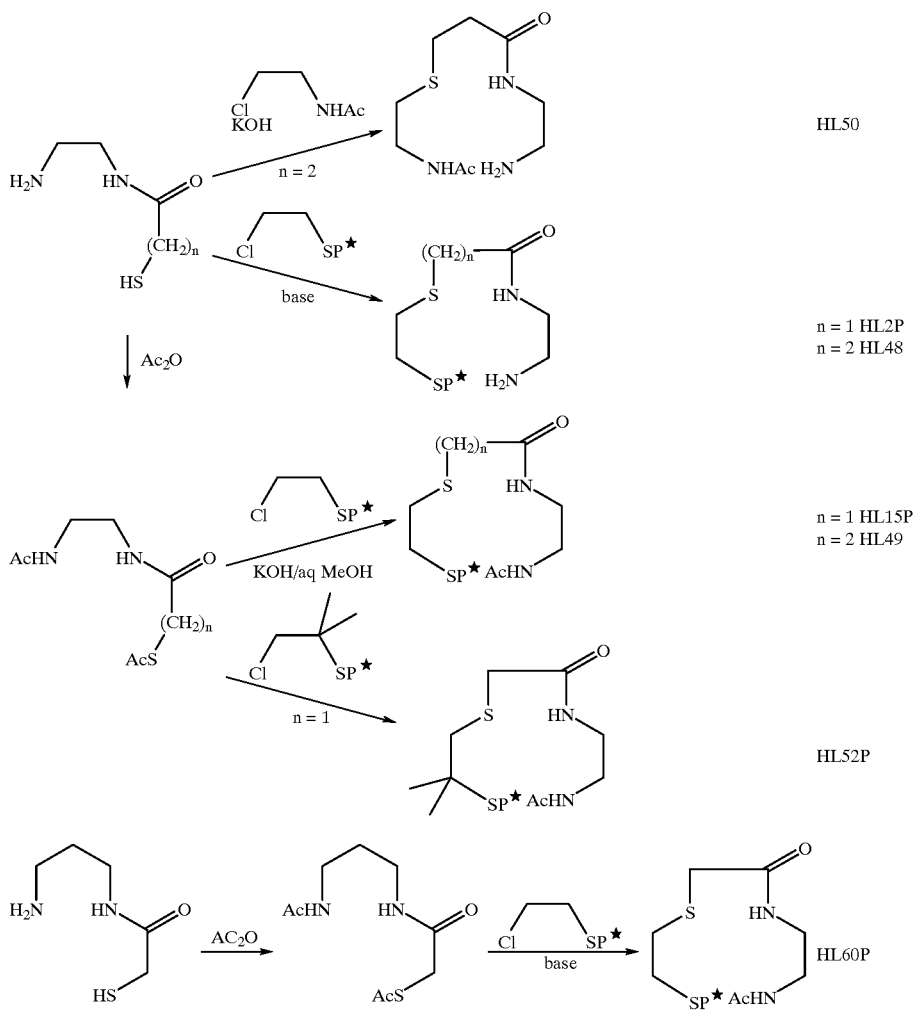
HL50
n = 1 HL2P
n = 2 HL48
n = 1 HL15P
n = 2 HL49
HL52P
HL60P
P★ = tetrahydropyranyl thiol protectng group
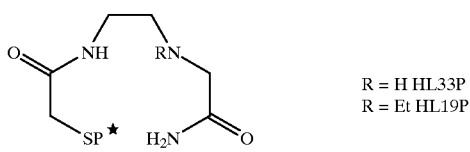
R = H HL33P
R = Et HL19P

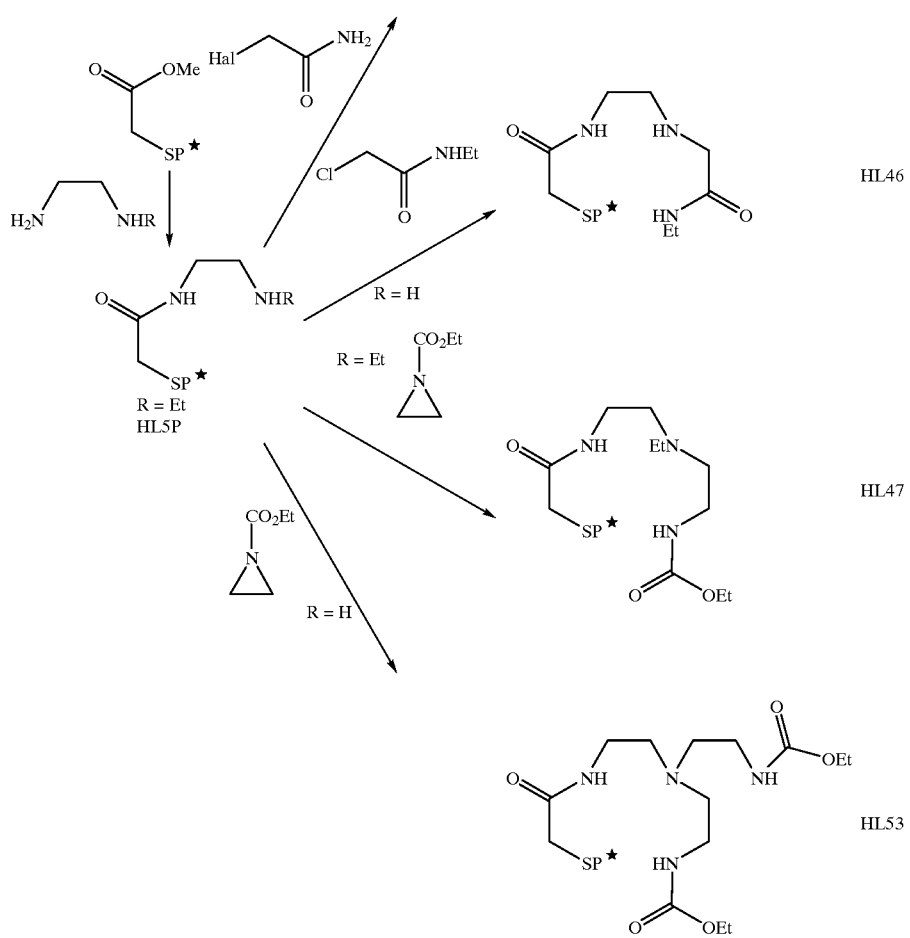
P* = tetrahydropyranyl thiol protecting group
SCHEME 3
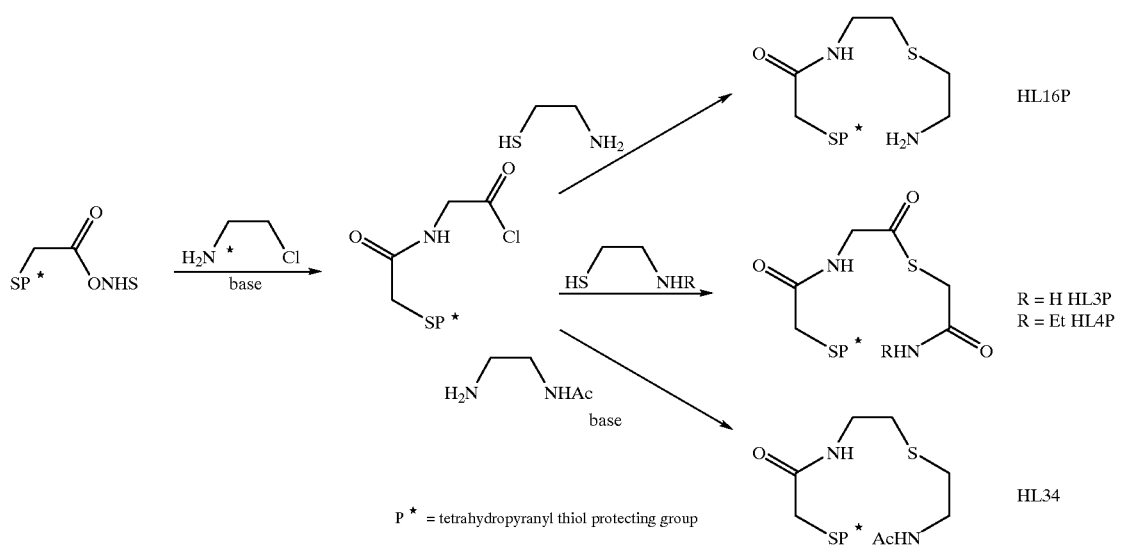
P* = tetrahydropyranyl thiol protecting group

SCHEME 4
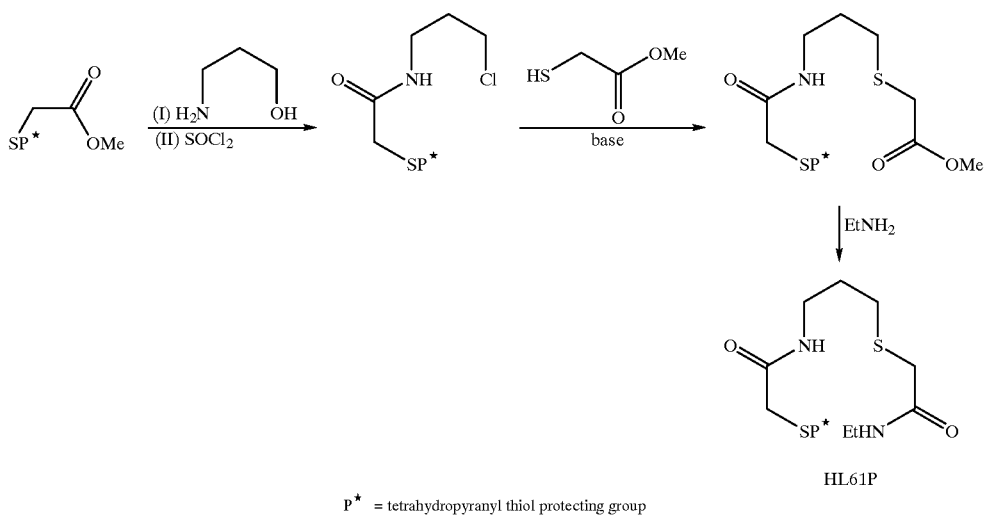
P* = tetrahydropyranyl thiol protecting group
SCHEME 5
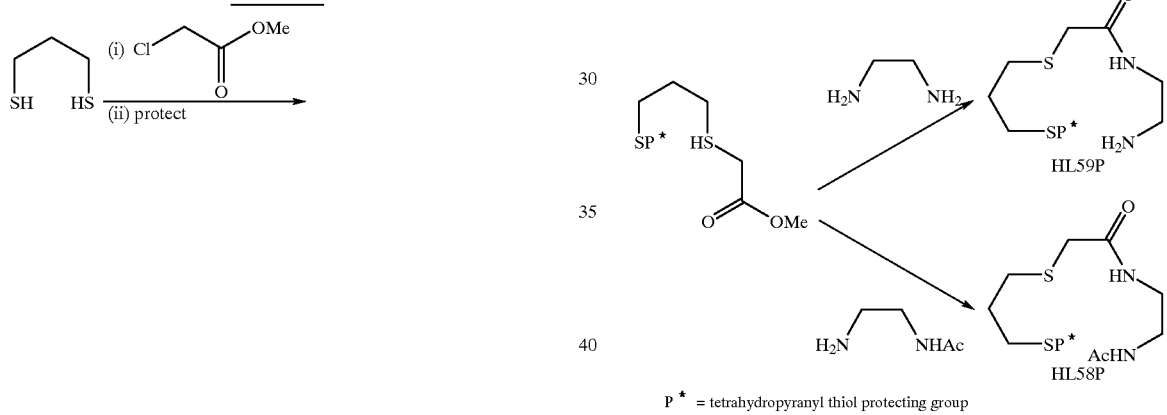
P* = tetrahydropyranyl thiol protecting group

SCHEME 6

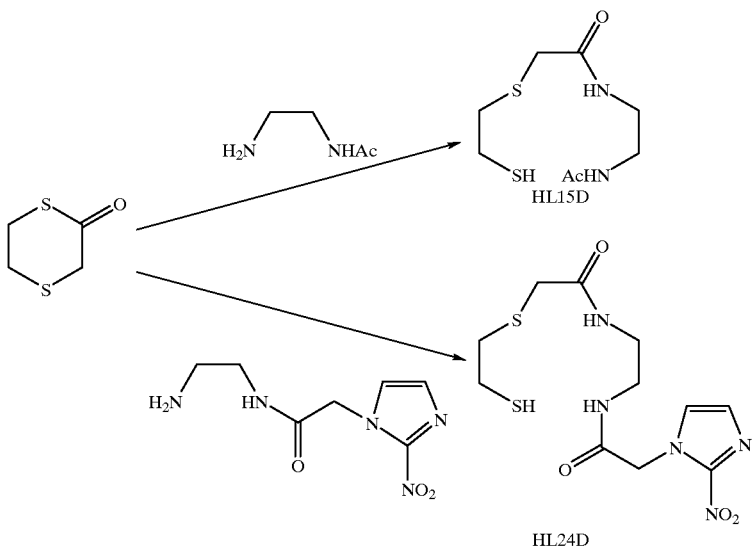

EXPERIMENTAL

Abbreviations
Acm=acetamidomethyl
DCCI=dicyclohexylcarbodiimide
MeCN=acetonitrile
TFA=trifluoroacetic acid
MeOHd$_4$=Deuterated methanol
CDCl$_3$=" chloroform

Synthesis of HL8P
This was synthesised according to standard peptide synthetic procedures.

Spectral Data

Mass spectrum shows parent ion (M+H$^+$) at 320.
Theoretical chemical mass is 319.

$^1$H NMR (MeOHd$_4$): δ4.5 (1H, SCH-NH,d); 4.2 (1H, SCHNH,d); 4.15 (1H,H$_2$NCH,t); 3.9 (2H,NHCH$_2$C=O,s); 3.5 (2H,Me$_2$NCH$_2$CH$_2$,t); 3.2 (2H,Me$_2$NCH$_2$,s); 3.1 (1H, CHCH$_2$S,dd); 2.8 (1H,CHCH$_2$ S,dd); 2.85 (6H, NMe$_2$,s); 1.9 (3H,NHC=OCH$_3$,s) ppm.

Synthesis of HL7P
This was synthesised according to standard synthetic peptide procedures.

Spectral Data

Mass spectrum shows parent ion (M+H$^+$) at 362.
Theoretical chemical mass is 361.

$^1$H NMR (MeOHd$_4$): δ5 4.5 (1H,SCHNH,d); 4.3 (1H, SCHNH,d); 4.2 (1H, NHCHC=O,t); 3.7(1H,C=ONHCH$_2$, m); 3.5 (1H,C=ONHCH$_2$,m); 3.3 (2H,SCH$_2$C'O,s); 3.27 (2H,CH$_2$NMe$_2$,t); 2.92 (6H,NMe$_2$,s); 2.9 (2H,CH$_2$NH$_2$,t); 2.0 (3H,NHC=OCH$_3$,s); 1.9 (2H,CHCH$_2$,CH$_2$,brm); 1.7 (2H,H$_2$NCH$_2$CH$_2$,brm); 1.5 (2H,H$_2$NCH$_2$CH$_2$CH$_2$,brm) ppm.

Synthesis of HL9P
This was synthesised according to standard synthetic peptide procedures.

Spectral Data

Mass spectrum shows parent ion (M+H$^+$) at 277.
Theoretical chemical mass is 276.

$^1$H NMR (MeOHd$_4$): δ4.4 (2H,SCH$_2$NH,s); 3.9 (2H, NHCH$_2$C=O,s); 3.5 (2H,NHMeCH$_2$CH$_2$,t); 3.35 (2H, C=OCH$_3$S,s); 3.15 (2H,CH$_2$NHCH$_3$,t); 2.7(3H,NHCH$_3$,s); 1.95 (3H,C=ONHCH$_3$, s) ppm.

Synthesis of HL10P
HL10P was synthesised via the reaction of 1-(2-aminoethyl)-2-nitroimidazole with S-benzoylmercaptoacetic acid-β-alanine-N-hydroxy succinimide active ester.

S-benzoylmercaptoacetic acid-β-alanine-N-hydroxyl succinimide active ester (A) was synthesised in 3 steps using standard chemical procedures (see Scheme I):

i) mercaptoacetic acid+benzoyl chloride→S-benzoyl mercaptoacetic acid;

ii) S-benzoylmercaptoacetic acid+β-alanine in the presence of DCCI→S-benzoylmercaptoacetic acid-β-alanine;

iii) S-benzoylmercaptoacetic acid-β-alanine+N-hydroxy succinimide in the presence of DCCI→product (A).

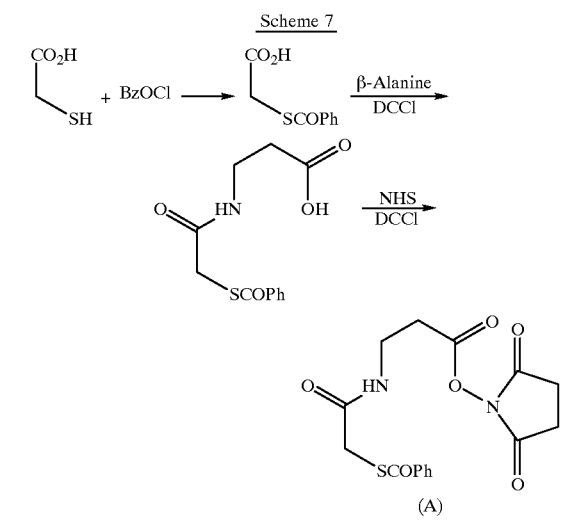

Scheme 7

1-(2-aminoethyl)-2-nitroimidazole (B) was synthesised in 2 steps (Scheme 8):

i) 2-nitroimidazole+2-Bromoethylphthalimide→1-(ethylphthalimide)-2-nitroimidazole.

ii) 1-(ethylpthalimide)-2-nitroimidazole refluxed with methylamine gives 1-(2-aminoethyl)-2-nitroimidazole).

Scheme 8

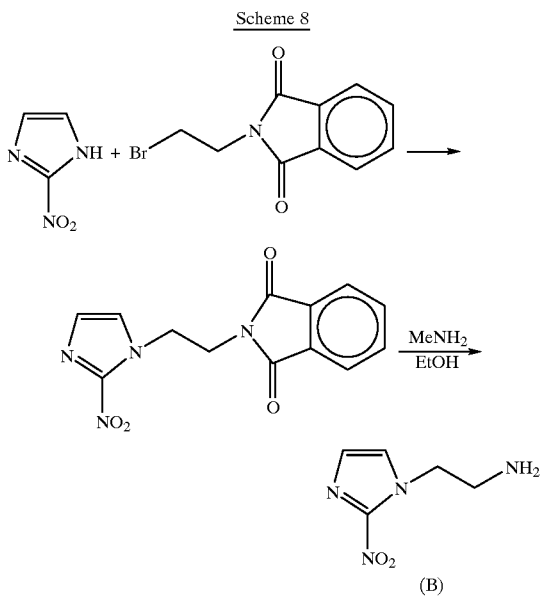

The active ester (A) (200 mg 0.567 mmol) was dissolved in chloroform (5 ml). The amine (B) (90 mg, 0.478 mmol) was dissolved in acetonitrile (5 ml). To a stirred solution of the ester was added the amine solution dropwise over 10 minutes. The solution was left to stir for 18 hours. The required product was isolated by preparative HPLC as an oil which can be recrystallised from methanol to give a white solid (Yield=90 mg, 0.23 mmol, 40%).

HPLC Conditions
Column: PRP-1 10 mm×25 cm
Flow rate : 2.5 mls min$^{-1}$
Eluant A : 5% acetic acid
Eluant B : acetonitrile
Gradient : 20 to 100% B over 18 minutes
Retention time of product is 11 minutes.
Spectral Data
A) S-benzoylmercaptoacetic acid-β-alanine-N-hydroxy succinimide ester
$^1$H NMR (CDCl$_3$): δ8.0 (2H,Ph,ortho-H,d); 7.7 (1H,Ph-para H,t); 7.55 (2H,Ph meta-H,t); 7.0 (1H,NHCO,br); 3.8 (2H, C=OCH$_2$SC=O,s); 3.7 (2,H,NHCH$_2$CH$_2$,m); 2.9 (2H,CH$_2$CH$_2$ C=O,t); 2.8 (4H, C=O CH$_2$CH$_2$ C=O,s) ppm.
B) 1-(2-aminoethyl)-2-nitroimidazole
$^1$H NMR (MeOHd$_4$): δ7.55 (1H, imidazole-H,s); 7.2 (1H, imidazole-H,s); 4.75 (2H,CH$_2$CH$_2$NH$_2$,t); 3.45 (2H, CH$_2$NH$_2$,t) ppm.
C) HL10P
$^1$H NMR (MeOHd$_4$): δ7.95 (2H, Ph,ortho-H,d); 7.65 (1H, Ph,para-H,t); 7.5 (2H,Ph,meta-H,t); 7.4 (1H, imidazole-H, s); 7.1 (1H, imidazole-H,s); 4.5 (2H,N—CH$_2$CH$_2$,t); 3.8 (2H,C=OCH$_2$S,t); 3.6(2H,NHCH$_2$CH$_2$C=O ,t); 3.4 (2H, C=ONHCH$_2$CH$_2$,t); 2.35 (2H,CH$_2$CH$_2$C=O,t) ppm.
Synthesis of HL11P
This was synthesised via the reaction of HL8P with 1-(2,3-epoxypropyl)-2-nitroimidazole$^{(8)}$.

1-(2,3-epoxypropyl)-2-nitroimidazole (57 mg, 0.34 mmol) was dissolved in methanol (1 ml) and water (0.5 ml). HL8P (100 mg, 0.31 mmol) was similarly dissolved. The two solutions were mixed and 4 drops of triethylamine added to adjust the pH to 10.0. The mixture was allowed to stir at room temperature for 72 hours, then evaporated to dryness and redissolved in water/0.1% TFA followed by HPLC purification to give a white solid. (Yield 35 mg, 0.07 mmol, 23%).
HPLC conditions
Column : Novapak C-18 300 mm×8 mm
Flow : 2 ml min$^{-1}$
Eluant A : 0.1% TFA
Eluant B : 1:1 MeCN/0.1% TFA
Gradient : 0 to 41% B over 20 minutes,
minutes at 41% B
Spectral Data
$^1$H NMR (MeOHd$_4$): δ7.5 (1H,imidazole-H,s); 7.15 (1H, imidazole-H,s); 4.65 (2H,N—CH$_2$, m); 4.5 (1H,SCHNH,d); 4.4 (1H,CHOH,m); 4.25 (1H,SCH$_2$NH,d); 4.2 (1H,CH—NH—,t); 3.9 (2H,NHCH$_2$,C=O,s); 3.7 (2H,CH$_2$NHCH,d); 3.6 (4H,Me$_2$NCH$_2$CH$_2$,dt); 3.25 (6H,NMe$_2$,s); 3.15 (1H, CHCH$_2$S,dd); 2.9 (1H,CHCH$_2$S,dd); 2.0 (3H,NHC=OCH$_3$, s) ppm.
Synthesis of HL12P
This was synthesised in a similar method to HL11P but using the 3-nitrotriazole derivative in place of 2-nitroimidazole and HPLC column=PRP-1 10 mm×250 mm.
Retention time of product is 13.6 minutes.
Spectral data
$^1$H NMR (MeOHd$_4$): δ8.65 (1H, triazole H,s); 4.7 (2H, N—CH$_2$,br); 4.5 (1H,CHOH,m); 4.4 (2H,CHCH$_2$NH,m); 4.25 (2H,SCH$_2$NH,m); 3.9 (2H,NHCH$_2$C=O,s); 3.7 (2H, CH$_2$NHCH,br); 3.6 (4H,Me$_2$NCH$_2$CH$_2$,dt) 3.25 (6H,NMe$_2$, s); 3.15 (1H,CHCH$_2$S,dd); 2.9 (1H,CHCH$_2$S,dd), 2.0 (3H, NHC=OCH$_3$,s) ppm.
Synthesis of HL22P
This was synthesised using a procedure similar to that used for HL11P employing 0.18 mmol of ligand and 0.2 mmol of epoxide.
HPLC conditions as HL11P except gradient is 0 to 100% B over 20 minutes, then 5 minutes at 100% B and column used is Hamilton PRP-1 10 mm×250 mm.
Retention time of product is 23.6 minutes.
Spectral data
$^1$H NMR (MeOHd$_4$): δ7.45 (1H, imidazole-H,t); 7.15 (1H,imidazole-H,s); 4.95 (1H,S—CH—O,t); 4.7 (1H, N—CH—CHOH,dd); 4.4 (1H,N—CH—CHOH,dd); 4.3 (1H,CH—OH,m); 4.0 (1H,S—CH—O—CH,m); 3.5 (2H, C=ONHCH,t) 3.45 (1H,SCH—O—CH,m); 3.25 (2H, SCH$_2$C=O,s); 3.2 (2H,NHCH$_2$,CHOH,m); 3.15 (2H, NHCH$_2$,m); 2.8 (4H,SCH$_2$CH$_2$S,m); 1.8 (2H,CH$_2$CHS,m); 1.5 (4H,CH$_2$CH$_2$CH$_2$,m)ppm.
$^{13}$C NMR (MeOHd$_4$): δ175.1, 139.2, 129.3, 84.6, 67.6, 66.4, 54.9, 51.8, 38.6, 36.6, 35.0, 33.3, 32.0, 29.4, 27.5, 26.2, 23.4 ppm.
Synthesis of HL23P
This was synthesised according to the procedure for HL24P but using HL7P as the ligand.
HPLC Conditions
Column=PRP-1 10×250 mm
Gradient=0 to 50% B over 20 mins.
Flow=2.5 ml min$^{-1}$
Eluant A=0.1% TFA
Eluant B=1:1 0.1% TFA/MeCN
Retention time of product=16.4 minutes
Spectral Data
$^1$H NMR (MeOHd$_4$): δ7.45 (1H, imidazole-H,s); 7.15 (1H,imidazole-H-s); 5.15 (2H,N—CH$_2$); 4.5 (1H,SCH—NH,d); 4.3 (1H,SCHNH,d); 4.2 (1H,NHCHC=O,m); 3.7 (1H,CH$_2$NH$_2$,m); 3.5 (1H,CH$_2$NH$_2$,m); 3.3 (2H, SCH$_2$C=O,s); 3.2 (4H,CH$_2$CH$_2$,NMe$_2$,m); 2.9 (6H,N(Me)$_2$,s); 2.0 (3H,NHC=OCH$_3$,s); 1.8 (2H,CHCH$_2$CH$_2$,m); 1.6 (2H,H$_2$NCH$_2$CH$_2$,brm); 1.5 (2H,HN$_2$,CH$_2$CH$_2$CH$_2$, brm) ppm $^{13}$C NMR (MeOHd$_4$): ppm 176.3, 173.8, 168.9, 130.3, 129.2, 59.5, 56.7, 53.7, 44.9, 42.7, 40.9, 36.6, 35.2, 32.6, 30.8, 24.8, 23.5.

Synthesis of HL24P

HL2P (50 mg, 0.18 mmol) was dissolved in acetonitrile (1 ml). 1-(acetic acid)-2-nitroimidazole (31 mg, 0.18 mmol) was dissolved in acetonitrile (3 ml) and added to the HL2P solution and the mixture stirred. DCCI (60 mg, 0.29 mmol) dissolved in acetonitrile (2 ml) was added dropwise to the stirred solution over 10 minutes. The solution was left to stir at room temperature for 72 hours. The white precipitate which had appeared was filtered off and the product purified bypreparative HPLC to give an oil. (Yield=40 mg=0.07 mmol, 50%).

HPLC conditions
Column : PRP-1 10 mm×25 cm
Flow : 2.5 ml min$^{-1}$
Gradient=0 to 100% B over 20 mins. 50% B for 5 mins
Eluant A : 0.1% TFA
Eluant B : MeCN
Retention time of product=20.8 mins.

Spectral data $^1$H NMR (MeOHd$_4$) δ8.3 (1H,NHC=O,br); 7.45 ( H, imidazole-H,s); 7.15 (1H,imidazole-H,s); 5.15 (2H, N—CH$_2$,s); 4.9 (1H,S—CH—O,brm); 4.0 (1H, CH—O—CH,m); 3.5 (1H,CH—OCH,m); 3.4 (4H, NCH$_2$CH$_2$N,br); 3.2 (2H,SCH$_2$C=O,s); 2.8 (4H, SCH$_2$CH$_2$S,m); 1.8 (2H, CH$_2$CH—S,m); 1.5 (4H, ring CH$_2$,m)ppm.

$^{13}$C NMR(MeOHd$_4$): δ174.0, 130.1, 129.2, 84.6, 66.5, 53.6, 41.0, 37.0, 35.0, 33.3, 32.0, 27.5 23.5 ppm.

Synthesis of HL29P

This was synthesised according to standard peptide procedures.

Spectral data

Mass spectrum shows parent ion at (M-H$^+$)=505
Theoretical chemical mass=505

$^1$H NMR (MeOHd$_4$): δ7.35 (15H,Ph$_3$,m); 4.3 (1H, H$_3$CCH,q); 3.6 (2H,CH$_2$NHC=O,t); 3.4 (1H, H$_2$NCH,m); 3.2 (2H,CH$_2$N(Me)$_2$,t); 2.8 (6H, N(CH$_3$)$_2$,s); 2.7 (1H, CH$_2$SCPh,dd); 2.6 (1H, CH$_2$SCPh$_3$,dd); 1.4 (3H,CH—CH$_3$, d)ppm.

Synthesis of HL40P

This was synthesised using a similar procedure as that for HL24P.

Retention of required product=20.8 minutes.

Spectral data $^1$H NMR (MeOHd$_4$): δ7.45 (1H,imidazole-H,s); 7.15 (1H,imidazole-H,s); 5.15 (2H,N—CH$_2$,s); 4.95 (1H, SCH—O,br); 4.0 (1H,O—CH$_2$, m); 3.5 (1H,O—CH$_2$,m); 3.4 (4H, CH$_2$SCH$_2$,dt); 3.3 (1H,CH$_2$SCHO,d) 3.2 (1H,CH$_2$SCHO,d) 2.7 (4H, NHCH$_2$NHCH$_2$,dt); 1.8 (2H,cyclohexyl H,m); 1.6 (4H,cyclohexyl H,m) ppm.

$^{13}$C NMR (MeOHd$_4$); δ173.5, 168.9, 130.1, 129.1, 84.5, 66.6, 53.6, 41.3, 37.0, 35.5, 33.9, 27.5, 26.8, 23.4 ppm.

Synthesis of HL64

This was synthesised using the active ester as employed in the synthesis of HL1OP. 3-(2-aminoethyl)amino-2-hydroxyl-propyl-1-(2-nitroimidazole) was synthesised from 1-(2,3-epoxypropyl)2-nitroimidazole and mono protected ethylene diamine, using standard chemistry. i.e.

Scheme 9

Spectral data $^1$H NMR (MeOHd$_4$): δ7.9 (2H, ortho-H,d); 7.7 (1H, para-H,t); 7.6 (2H, meta-H,t); 7.4 (1H, imidazole-H,s); 7.1 (1H, imidazole-H,s); 4.5 (1H, N—CH$_2$,br); 4.2 (2H, N—CH$_2$,CH—OH,br); 3.8 (2H, CH$_2$SCOPh,s); 3.4 (4H, NHCH$_2$CH$_2$NH,br); 3.2 (2H, NCH$_2$CH$_2$C=O,t); 2.95(2H, CH$_2$NHCH$_2$,br); 2.8 (1H,CH$_2$NHCH$_2$,br); 2.4 (2H, CH$_2$C=O, t) ppm.

Radiolabelling
Analytical Methods
Thin Layer Chromatography:
Whatman No. 1 paper eluted with 50% aqueous acetonitrile.
Reduced hydrolyzed Tc: R$_f$=0.0
ITLC SG eluted with 0.9% aqueous NaCl.
Free pertechnetate: R$_f$=1.0
% complex=100−free pertechnetate−reduced hydrolyzed Tc HPLC:
Hamilton PRP-1 column eluted at 2 ml/min
Gradient 100% pH 5.6 50 mM sodium acetate to 100% tetrahydrofuran over 17 minutes.

The Preparation of the Technetium Complexes of HL15, HL49, HL60 and HL70

Approximately 1 mg of one of the above compounds was weighed into a 10 ml vial and the vial was sealed and degassed and then one ml of water, 50 pi of an acidic solution (1:7 v/v glacial acetic acid: 0.2M hydrochloric acid) and 1.0 ml of a preparation of $^{99m}$Tc-gluconate complex were added to the vial. 1.0 ml of saline solution was then added to the vial and the reaction mixture was heated at 90° C. for twenty minutes, incubated at room temperature for 30 minutes and then analyzed. Nearly quantitative formation of the HL ligand-technetium complexes was indicated by TLC and HPLC.

HL15: HPLC r$_t$=4.6 min
HL49: HPLC r$_t$=4.5 min
HL60: HPLC r$_t$=4.4 min
HL70: HPLC r$_t$=4.7 min The Preparation of the Technetium Complex of HL41, and HL88

Approximately 10 mg of one of the above compounds was weighed into a 10 ml vial and the vial was sealed and degassed and then one ml of saline, 0.23 ml of 0.1M an aqueous NaOH, approximately 0.5 GBq of [$^{99m}$TcO4]$^-$ solution (one ml of generator eluate) and 0.2 ml of an aqueous solution of SnCl$_2$ (10 mg in 100 ml saline) were added to the vial. The vial was incubated at room temperature for 30 minutes and then analyzed. Nearly quantitative formation of the HL ligand-technetium complex was indicated by TLC and HPLC.

HL41: HPLC r$_t$=1.9 min
HL88: HPLC r$_t$=4.6 min

The Preparation of the Technetium Complex of HL41A and HL85

Approximately 1 mg of HL41A was weighed into a 10 ml vial which contained a disc of tin metal and the vial was sealed and degassed and then 5 ml of saline and one ml (approximately 0.25 GBq) of [$^{99m}$TcO(gluconate)$_2$]$^-$ solution were added to the vial. The vial was incubated at room temperature for 30 minutes and then analyzed. Nearly quantitative formation of the technetium complex was indicated by TLC and HPLC (HPLC $r_t$=4.8 min for HL41A complex)

(HPLC $r_t$=3.4 min for HL85 complex)

Plasma protein binding of Technetium Complexes

Human plasma protein binding was determined by ultrafiltration[9], such that the percentage of complex bound is an indicator of the affinity of binding.

The plasma protein binding figure obtained for a given compound is highly dependent on the method of determination used[10]. Thus equilibrium dialysis measurement may lead to higher PPB figures than those obtained via ultrafiltration due to longer incubation times. Use of serum rather than plasma may also underestimate the true extent of binding. There are also significant interspecies differences.

Red cell ghost (RCG) uptake

The ability of the complex to cross or enter biological membranes was demonstrated by incubation of the complex with human erythrocyte ghosts[11, 12] followed by filtration of the ghost suspension and assessment of the membrane-associated activity.

RCG uptake is determined by incubation of a fixed amount of labelled complex with a range of ghost concentrations. The percentage of labelled complex added to the incubate is calculated for each ghost concentration to yield a single uptake figure expressed as %/mg protein. Non-permeable complexes such as $^{99m}$Tc-DTPA are excluded from the ghosts.

| Technetium Complex | PPB % bound | RCG uptake %/mg protein |
| --- | --- | --- |
| HL15P | 0 | 1.6 |
| HL41 | 27 | 2.6 |
| HL41A | 14 | 7.7 |
| HL49 | 18 | 3.6 |
| HL60P | 0 | 1.1 |
| HL70P | 0 | 2.1 |
| PnAO | 75 | 6.7 |
| BAT | 62 | Not available |

Hypoxic and oxic binding of $^{99m}$Tc labelled compounds to cells in vitro

V79-379A Chinese hamster cells were harvested from exponential suspension culture and resuspended at $1.1 \times 10^6$ cells cm$^{-3}$ in Eagle's MEM. 20 cm$^3$ of cells were transferred to small spinner vessels and gassed with either air+5% CO$_2$ (oxic) or nitrogen+5% CO$_2$ (Hypoxic) at 37° C. After 30 minutes, between 0.5 cm$^3$ and 1 cm$^3$ of $^{99m}$Tc labelled compound was added. At timed intervals 1 cm$^3$ of cell suspension was withdrawn from each flask and chilled on ice in small polystyrene centrifuge tubes. The cells were centrifuged and washed three times in ice-cold medium (Eagle's MEM) to give constant counts in the cell pellet. The pellets were counted in LKB 1282 Compugamma counter. The initial supernatant was diluted 1 in 100 with saline and 1 cm$^3$ was counted. All samples were counted at the end of the incubation period and counts have been corrected for decay during counting but not for decay during incubation.

Attempts were made to decrease the amount of non-specific binding by incubating the cell samples in a large volume of medium for one hour at 37° C. under oxic conditions. Although this treatment reduced the total counts in both hypoxic and oxic cell pellets, it did not improve the differential.

In vitro binding of HL11P to V79 cells

| Time (hrs) | Oxic pellet (cpm) | Hypoxic pellet (cpm) | Oxic SN (cpm/ml) | Hypoxic SN (cpm/ml) | Hypoxic: oxic ratio |
| --- | --- | --- | --- | --- | --- |
| 0.5 | 0.42 | 2.15 | 25.1 | 22.2 | 5.79 |
| 1.0 | 0.71 | 1.85 | 24.9 | 22.3 | 2.91 |
| 2.0 | 0.99 | 3.33 | 25.5 | 22.2 | 3.86 |
| 3.0 | 1.18 | 3.72 | 25.6 | 22.4 | 3.60 |
| 4.0 | 1.40 | 6.22 | 26.0 | 22.8 | 5.07 |
| 5.0 | 1.63 | 4.70 | 25.7 | 22.7 | 3.26 |

SN = supertantant
cell cpm are x10$^{-5}$
supernatant cpm are x10$^{-7}$
sample size is 10$^6$ cells per pellet Preparation of N-(2-Ethylaminoethyl)-tetrahydropyran-2-ylthioacetamide [HL 5P]

Methyl tetrahydropyran-2-ylthioacetate

Dihydropyran (19 g, 230 mmol) was added dropwise to a solution of methyl mercaptoacetate (20 g, 188 mmol) in anhydrous ether (40 cm$^3$) cooled in ice. Hydrogen chloride was passed into this solution until it began to feel warm and then the mixture was left to stand at room temperature overnight. Volatile components were removed under reduced pressure (50 C at 20 mmHg) to give the methyl tetrahydropyran-2-ylthioacetate in essentially quanitative yield. This material was sufficiently pure to be used without further purification.

$\delta_H$(CDCl$_3$; 270 MHz) 1.40–1.95(6H, broad envelope of overlapping resonances), 3.09(1H, d, J=15 Hz), 3.29(1H, d, J=15 Hz), 3.39(1H, m), 3.58(3H, s), 3.92(1H, m), 4.91(1H, m).

$\delta_C$(CDCl$_3$) 20.8(t), 25.2(t), 30.3(t), 30.9(t), 52.0(q), 63.6 (t), 81.3(d), 170.8(s).

N-[2-(N'-Ethylamino)ethyl]-tetrahydropyran-2-ylthioacetamide

N-Ethylethylenediamine (10 g, 113 mmol) was added to methyl tetrahydropyran-2-ylthioacetate (21.58 g, 113 mmol) and the mixture heated at 70° C. for 2 h. Methanol was then removed from the reaction mixture in vacuo to give the N-[2-(N'-ethylamino)ethyl]-tetrahydropyran-2-ylthioacetamide (27.6 g, 99%) in a good state of purity.

$\delta_H$(CDCl$_3$; 270 MHz) 1.04(3H, t, J=7 Hz), 1.40–1.95(6H, broad envelope of overlapping resonances), 2.60(2H, q, J=7 Hz), 2.65(1H, br s), 2.70(2H, t, J=6 Hz), 3.17(1H, d, J=16 Hz), 3.34(2H, m), 3.33(1H, d, J=16 Hz), 3.44(1H, m), 3.95(1H, m), 4.76(1H, m), 7.40(1H,br s).

$\delta_C$(CDCl$_3$) 14.7(q), 21.5(t), 25.0(t), 30.8(t), 34.2(t), 38.9 (t), 43.3(t), 47.9(t), 65.1(t), 82.8(d), 169.4(s).

Preparation of N-(2-Aminoethyl)-2-(2-tetrahydropyranylthio)ethyl-thioacetamide [HL 2P]

N-(2-Aminoethyl)-2-(tetrahydropyran-2-ylthio)ethylthioacetamide 2-(2'-Chloroethylthio)tetrahydropyran$^1$ (1.46 g, 8.1 mmol), N-(2-aminoethyl)-mercaptoacetamide$^2$ (1.2 g, 9 mmol), potassium hydroxide (0.56 g, 10 mmol) and methanol (10 cm$^3$) were mixed together and the mixture heated at 75° C. under reflux for 30 min. After filtering, the solvent was removed in vacuo to give a residue which was taken up into chloroform (40 cm$^3$) and then extracted with water (2×30 cm$^3$). The chloroform solution was then dried (MgSO$_4$), filtered, and the solvent removed under reduced pressure to give the crude product, which was shown by n.m.r. spectroscopy to contain the desired ligand as the dominant species. A portion of this material was purified, firstly by chromatography on silica using a mixture of ethyl acetate, methanol, and aqueous ammonia (90:8:2) as the eluant and then by reverse phase h.p.l.c. using aqueous acetonitrile as the eluant. N-(2-Aminoethyl)-2-(tetrahydropyran-2-ylthioethyl)thioacetamide was obtained as a colourless viscous oil.

$\delta_H$(CDCl$_3$; 270 MHz) 1.45–1.93(6H, broad envelope of overlapping resonances), 2.70–2.86(6H, broad envelope of overlapping resonances), 3.21(2H, s), 3.28(2H, q, J=6 Hz), 3.44(2H, m), 3.99(1H, m), 4.83(1H, m), 7.27(1H, br s).

$\delta_C$(CDCl$_3$) 21.5(t), 25.3(t), 30.0(t), 31.1(t), 33.4(t), 35.9 (t), 41.2(t), 42.2(t), 64.5(t), 82.5(d), 169.0(s).

1. D. T. Witiak and M. C. Lu, *J. Org. Chem.*, 1970, 35, 4209
2. P. J. Toscano and L. G. Marzilli, *Inorg. Chem.*, 1983, 22, 3342

Preparation of 2-(Tetrahydropyran-2-ylthioacetamido) ethylthioacetamide [HL 3P]

N-(2-Chloroethyl)-(2-tetrahydropyranyl)thioacetamide

To a solution of succinimidoyl tetrahydropyran-2-ylthioacetate (0.5 g, 2 mmol) in acetonitrile (10 cm$^3$) was added 2-chloroethylamine hydrochloride (0.55 g, 4 mmol) and triethylamine (0.51 g, 4 mmol). The mixture was allowed to stir overnight, filtered, and the volatile components removed under reduced pressure to give a residue which was taken up into ethyl acetate (20 cm$^3$) and the extracted with water (2×15 cm$^3$). The resulting solution was dried (MgSO$_4$), filtered, and the solvent removed under reduced pressure to give the N-(2-chloroethyl)-tetrahydropyran-2-ylthioacetamide in essentially quantitative yield. This material was in a sufficiently pure state to used without further purification.

$\delta_H$(CDCl$_3$; 270 MHz) 1.43–1.93(6H, broad envelope of overlapping resonances), 3.21(1H, d, J=16 Hz), 3.36(1H, d, J=16 Hz), 3.48(1H, m), 3.55(4H, m), 3.99(1H, m), 4.75(1H, m), 7.55(1H, br s).

$\delta_C$(CDCl$_3$) 21.6(t), 24.9(t), 30.8(t), 34.2(t), 41.2(t), 43.3 (t), 65.5(t), 83.0(d), 169.7(s)

2-(Tetrahydropyran-2-ylthioacetamido)ethylthioacetamide

A mixture of N-(2-chloroethyl)-tetrahydropyran-2-ylthioacetamide (0.45 g, 2 mmol), mercaptoacetamide (0.19 g, 2.1 mmol), potassium hydroxide (0.12 g, 2.1 mmol) and methanol (10 cm$^3$) was heated at 75° C. for 30 min and then allowed to cool. After filtering, the organic solvent was removed under reduced pressure to give a the crude product as a pale yellow oil. This material was purified firstly by chromatography on silica using a mixture of ethyl acetate, and methanol (90:10) as the eluant and then by reverse phase h.p.l.c. using aqueous acetonitrile as the eluant. 2-(Tetrahydropyran-2-ylthioacetamido)ethylthioacetamide (120 mg, 20%) was isolated as a viscous oil.

$\delta_H$(CDCl$_3$; 270 MHz) 1.47–1.96(6H, broad envelope of overlapping resonances), 2.68(2H, t, J=7Hz), 3.18(2H, s), 3.19(1H, d, J=16 Hz), 3.36(1H, d, J=16 Hz), 3.43(2H, q, J=7 Hz), 3.48(1H, m), 3.98(1H, m), 4.74(1H, m), 6.14(1H, br s), 6.86(1H, br s), 7.41(1H, br s).

$\delta_C$(CDCl$_3$) 21.8(t), 25.1(t), 31.0(t), 32.3(t), 34.6(t), 35.0 (t), 38.5(t), 65.6(t), 83.2(d), 169.9(s), 172.0(s).

Preparation of N-Ethyl-2-(2-tetrahydropyranylthioacetylamino)ethyl thio-acetamide [HL 4P]

N-Ethyl-mercaptoacetamide

An aqueous solution of ethylamine (50 cm$^3$, 70%) was added to methyl thioglycolate (5.3 g, 50 mmol) in methanol (5 cm$^3$) and the solution allowed to stir overnight. Removal of the solvent under reduced pressure (50° C. at 20 mmHg) left the N-ethyl-mecaptoacetamide, as a colourless liquid, in essentially quantitative yield. This material was sufficiently pure to be used without further purification.

$\delta_C$(MeOH) 13.8(q), 27.5(t), 34.6(t), 171.6(s).

N-Ethyl-2-(tetrahydropyran-2-ylthioacetamido) ethylthioacetamide

A mixture of N-(2-chloroethyl)-tetrahydropyran-2-ylthioacetamide (0.75 g, 3.4 mmol), N-ethyl-mercaptoacetamide (0.40 g, 3.4 mmol), potassium hydroxide (0.28 g, 5 mmol) and methanol (5 cm$^3$) was heated under reflux for 40 min and then allowed to cool. After filtering the organic solvent was removed under reduced pressure to give the crude product as a viscous oil, which was shown by n.m.r. spectroscopy to contain the desired ligand as the major product. A portion of this material was purified, firstly by chromatography on alumina using a mixture of ethyl acetate, and methanol (98:2) as the eluant and then by reverse phase h.p.l.c. using aqueous acetonitrile as the eluant. N-Ethyl-2-(tetrahydropyran-2-ylthioacetamido) ethylthioacetamide was isolated as a white solid. Found: C, 48.78; H, 7.87; N, 8.88. C$_{13}$H$_{24}$N$_2$O$_3$S$_2$ requires C, 48.72; H, 7.55; N, 8.74%.

$\delta_H$(CDCl$_3$; 270 MHz) 1.09(3H, t, J=7 Hz), 1.48–1.92(6H, broad envelope of overlapping resonances), 2.65(2H, t, J=6 Hz), 3.17(2H, s), 3.18–3.28(2H, m), 3.18(1H, d, J=16 Hz), 3.34(1H, d, J=16 Hz), 3.41(2H, q, J=6 Hz), 3.46(1H, m), 3.98(1H, m), 4.79(1H, m), 7.18(1H, br s), 7.59(1H, t, J=6 Hz).

$\delta_C$(CDCl$_3$) 14.4(q), 21.5(t), 24.9(t), 30.7(t), 32.1(t), 34.1 (t), 34.3(t), 35.2(t), 38.4(t), 65.2(t), 82.7(d), 168.6(s) 169.7 (s).

Preparation of Bis-{N-2-[(N'-ethyl) carbamoylmethylthio] ethyl}-carbamoylmethyl disulphide [HL 4PSS]

Methyl 2-(bromoacetylamino)ethylthioacetate

Bromoacetic acid (4.9 g, 35 mmol) was added in portions to a stirred solution of 2-aminoethanethiol hydrochloride (4.0 g, 35 mmol) and sodium bicarbonate (9.3 g, 110 mmol) in water (20 cm$^3$). The mixture was stirred at room temperature overnight and its acidity then adjusted to pH 1 with hydrochloric acid. The water was removed under reduced pressure to leave a viscous residue to which was added methanol (50 cm$^3$). The mixture was allowed to stand overnight and was then filtered and the product precipitated from the filtrate by the addition of acetone. The preciptitate was filtered off and dried to give the product (5.8 g) as a white crystalline solid, which was shown to be the hydrohalide salt of methyl 2-aminoethylthioacetate.

$\delta_H$(D$_2$O; 270 MHz) 2.96(2H, t, J=7 Hz), 3.26(2H, t, J=7 Hz), 3.49(2H, s), 3.77(3H, s).

$\delta$C (D$_2$O) 29.3(t), 32.9(t), 38.1(t), 53.3(q), 173.4(s).

A quantity of this material (1.8 g) was mixed with bromoacetyl chloride (1.9 g, 12 mmol) in acetonitrile (20 cm$^3$), and triethylamine (2.5 g, 25 mmol) was then added dropwise. The mixture was stirred until the reaction was complete and then filtered. Volatile components were removed from the filtrate to give a residue. This residue was dissolved in chloroform (50 cm$^3$) and the solution extracted with water (2×30 cm$^3$). The chloroform solution was then dried (MgSO$_4$), filtered, and the solvent removed under reduced pressure to give the methyl 2-(bromoacetylamino) ethylthioacetate (1.5 g). This material was used without further purification.

$\delta_C$(CDCl$_3$) 28.6(t), 31.6(t), 32.6/32.7(t), 38.0/38.3(t), 52.1 (q), 165.9/166.0(s), 170.5(s)

O-Ethyl-S-{N-[2-(methoxycarbonylmethylthio)ethyl] carbamoylmethyl} xanthate

Methyl 2-(bromoacetylamino)ethylthioacetate (1.2 g, 4.4 mmol) in acetone (15 cm$^3$) was added to a stirred solution of potassium 0-ethyl xanthate (1.0 g, 6.2 mmol) in acetone (1.0 g, 6.2 mmol). The mixture was stirred at room temperature for 30 min and then filtered. The solvent was removed from the filtrate under reduced pressure to give an oil which was then dissolved in chloroform (50 cm$^3$). The chloroform solution was extracted with water (2×30 cm$^3$), dried (MgSO$_4$), filtered, and the solvent removed under reduced pressure to give the desired product in a good state of purity. Further purification was achieved by flash chromatography on silica using ethyl acetate as the eluant. The O-Ethyl-S-(N-[2-(methoxycarbonylmethylthio)ethyl]-carbamoylmet hyl) xanthate (1.02 g, 75%) was obtained as a yellow oil.

$\delta_H$(CDCl$_3$; 270 MHz) 1.27(3H, t, J=7 Hz), 2.62(2H, t, J=6.5 Hz), 3.11(2H, s), 3.32(2H, q, J=6 Hz), 3.57(3H, s), 3.72(2H, s), 4.49(2H, q, J=7 Hz), 7.05(1H, br t).

$\delta_C$(CDCl$_3$) 13.3(q), 31.9(t), 32.7(t), 38.2(t), 38.9(t), 52.1 (q), 70.5(t), 166.7(s), 170.5(s), 212.4(s)

Bis-{N-2-[-(N'-ethyl)carbamoylmethylthio]ethyl} carbamoylmethyl} disulphide

The xanthate ester (400 mg) was added to an aqueous solution of ethylamine (20 cm$^3$, 70%) and the mixture allowed to stand overnight. Volatile components were then removed under reduced pressure and the resulting solid washed with acetone. The resulting solid was shown by n.m.r. spectroscopy to be bis-(N-(2-[(N'-ethyl) carbamoylmethylthio]ethyl)-carbamoylmethyl) disulphide (120 mg).

$\delta_H$(d$_6$-DMSO; 270 MHz) 0.74(6H, t, J=7 Hz), 2.36(4H, t, J=6.5 Hz), 2.79(4H, m), 2.82(4H,s), 3.00(4H, q, J=6.5 Hz), 3.20(4H, s), 7.73(2H, br t), 8.00(2H, br t, J=5 Hz).

$\delta_C$(d$_6$-DMSO) 14.7(q), 31.3(t), 33.8(t), 34.4(t), 38.7(t), 41.9(t), 168.0(s), 168.8(s)

Preparation of N-(2-Acetylaminoethyl)-2-(tetrahydropyran-2-ylthio)ethylthioacetamide [HL 15P]

S-[N-(2-Acetylaminoethyl)carbamoylmethyl] thioacetate

To a stirred solution of N-(2-aminoethyl)-mercaptoacetamide (2.91 g, 21.7 mmol) in water (20 cm$^3$) was added dropwise glacial acetic acid (7.0 g, 69 mmol). The reaction mixture was stirred overnight and the water evaporated under reduced pressure to leave a white slurry. This material was dissolved in the minimum of methanol (ca. 10 cm$^3$) and filtered. The filtrate was then slowly added to diethyl ether (100 cm$^3$), whereupon a white precipitate formed. This was filtered off and dried in air to give the S-[N-(2-acetylaminoethyl)carbamoylmethyl] thioacetate (3.1 g, 66%) as a white powder.

$\delta_H$(D2O; 270 MHz) 1.96(3H, s), 2.41(3H, s), 3.30(4H, m), 3.63(2H, s).

$\delta_C$(D2O) 24.5(q), 32.2(q), 35.5(t), 41.1(t), 41.7(t), 173.8 (s), 177.0(s), 201.9(s)

N-(2-Acetylaminoethyl)-2-(tetrahydropyran-2-ylthio) eth-ylthioacetamide 2-(2-Chloroethylthio)tetrahydropyran (1.94 g, 10.7 mmol), S-[N-(2-acetylaminoethyl)carbamoylmethyl] thioacetate (2 g, 9.5 mmol), potassium hydroxide (1.4 g, 25 mmol), methanol (10 cm$^3$) and water (5 cm$^3$) were mixed together and heated at 75° C. for 90 min. Volatile components were then removed under reduced pressure to leave a yellow viscous residue which was partitioned between dichloromethane (50 cm$^3$) and water (50 cm$^3$). The dichloromethane layer was separated, dried (MgSO$_4$), filtered, and the solvent removed under reduced pressure to leave the crude product as a pale yellow waxy solid. A sample of this material was purified firstly by chromatography on silica using a mixture of ethyl acetate, and methanol (96:4) as the eluant and then by reverse phase h.p.l.c. using aqueous acetonitrile as the eluant. The pure N-(2-acetylaminoethyl)-2-(tetrahydropyran-2-ylthio)ethylthioac etamide (0.25 g) was obtained as a white solid. Found: C, 48.55; H, 7.61; N, 8.77. C$_{13}$H$_{24}$N$_2$O$_3$S$_2$ requires C, 48.72; H, 7.55; N, 8.74%.

$\delta_H$(CDCl$_3$; 270 MHz) 1.44–1.93(6H, broad envelope of overlapping resonances), 1.93(3H, s), 2.68–2.84(4H, m), 3.19(2H, s), 3.35(4H, m), 3.44(1H, m), 3.99(1H, m), 4.82 (1H, m), 6.47(1H, br s), 7.35(1H, br s).

$\delta_C$(CDCl$_3$) 21.4(t), 23.0(q), 25.3(t), 30.0(t), 31.1(t), 33.3 (t), 35.7(t), 39.7(t), 39.8(t), 64.5(t), 82.5(d), 170.0(s), 171.1 (s).

Preparation of N-(2-Acetylaminoethyl)-2-mercaptoethylthioacetamide [HL 15D]

2-Oxo-1,4-dithiane[1] (1.34 g, 10 mmol) in dichloromethane (10 cm$^3$) was added dropwise to N-acetylethylenediamine (1.10 g, 11 mmol) in dichloromethane (15 cm$^3$) and the resulting solution stirred at room temperature under nitrogen for 1 h. The solvent was removed under pressure and the residue dissolved in a little dichloromethane (5–10 cm$^3$). The product was then precipitate by the slow addition of this solution to diethyl ether (150 cm$^3$). The precipitate was filtered and then dried in vacuo to give the N-(2-acetylaminoethyl)-2-mercaptoethylthioacetamide as a white powder (2.2 g, 93%). Found: C, 40.86; H, 6.69; N, 12.09. C$_8$H$_{16}$N$_2$O$_2$S$_2$ requires C, 40.66; H, 6.82; N, 11.85%. This material tended to oxidise to the corresponding disulphide if handled in air.

$\delta_H$(CDCl$_3$; 270 MHz) 1.93(3H, S), 2.64–2.78(4H, m), 3.18(2H, s), 3.33(4H, m), 7.10(1H, br s) 7.67(1H, br s).

$\delta_C$(CDCl$_3$) 23.0(q), 24.0(t), 35.5(t), 36.5(t), 39.4(t), 39.7 (t), 170.0(s), 171.2(s).

1. J. Larsen and C. Lenoir, *Synthesis,* 1989, 134

The preparation of N-[2-(2-aminoethylthio)ethyl]-tetrahydropyran-2-ylthioacetamide [HL 16P]

N-(2-Chloroethyl)-tetrahydropyran-2-ylthioacetamide (0.48 g, 2 mmol), 2-mercaptoethylamine hydrochloride (0.34 g, 3 mmol), potassium hydroxide (0.34 g, 6 mmol) methanol (5 cm$^3$) and water (1 cm$^3$) were mixed and heated at 75 C for 2 h. After cooling, 111acetone (50 cm$^3$) was added and the resulting mixture filtered. Volatile components were removed from the filtrate under reduced pressure to give a pale yellow residue. This material was purified firstly by chromatography on silica using a mixture of ethyl acetate, methanol, and aqueous ammonia (90:9:1) as the eluant and then by reverse phase h.p.l.c. using aqueous acetonitrile as the eluant. The purified N-[2-(2-aminoethylthio)ethyl]-tetrahydropyran-2-ylthioacetamid e (1 g, 32%) was obtained as a pale yellow oil.

$\delta_H$(CDCl$_3$; 270 MHz) 1.53–1.91(6H, broad envelope of overlapping resonances), 2.58(2H, t, J=6 Hz), 2.61(2H, t, J=6 Hz), 2.83(2H, t, J=6 Hz), 3.19(1H, d, J=16 Hz), 3.36(1H, d, J=16 Hz), 3.40(2H, q, J=6 Hz), 3.47(1H, m), 3.98(1H, m), 4.74(1H, m), 7.39(1H, br s).

$\delta_C$(CDCl$_3$) 21.9(t), 25.1(t), 31.1(t), 31.2(t), 34.6(t), 35.7 (t), 38.9(t), 41.0(t), 65.7(t), 83.3(d), 169.3(5).

Preparation of N-[2-(N'-ethyl-N'-carbamoylmethyl) aminoethyl]-tetrahydropyran-2-ylthioacetamide [HL 19]

Iodoacetamide (0.37 g, 2 mmol) was added to a solution of N-[2-(N'-ethylamino)ethyl]-tetrahydropyran-2-ylthioacetamide (0.5 g, 2 mmol) in methanol (5 cm$^3$) and the mixture stirred at room temperature overnight. $^{13}$C n.m.r. spectroscopy indicated that the reaction was approximately 50% complete. The volatile components were removed in vacuo and the product isolated by reverse phase h.p.l.c. using aqueous methanol as the eluant. N-[2-(N'-ethyl-N'-carbamoylmethyl)aminoethyl]-tetrahydropyran-2-ylthioacetamide (0.21 g, 34%) was obtained as a pale yellow viscous oil. M$^+$303.

$\delta_H$(CDCl$_3$; 270 MHz) 0.99(3H, t, J=7 Hz), 1.46–1.93(6H, broad envelope of overlapping resonances), 2.55(2H, q, J=7 Hz), 2.58(2H, t, J=6 Hz), 3.03(2H,s), 3.19(1H, d, J=16 Hz), 3.28(2H, q, J=6 Hz), 3.34(1H, d, J=16 Hz), 3.47(1H, m), 3.95(1H, m), 4.75(1H, m), 6.54(1H, br s), 7.23(1H, br s), 7.43(1H, br t, J=6 Hz).

$\delta_C$(CDCl$_3$) 11.4(q), 21.7(t), 24.9(t), 30.9(t), 34.5(t), 37.4 (t), 48.6(t), 53.4(t), 57.7(t), 65.7(t), 83.2(d), 169.6(s), 174.7 (s).

The Preparation of N-{2-[(2-mercaptoethylthio) acetylamino]ethyl}-(2-nitroimidazol-1-yl)acetamide [HL 24D]

N-(2-Aminoethyl)-(2-nitroimidazol-1-yl)acetamide 1,2-Diaminoethane (0.15 g, 2.5 mmol) was added to ethyl (2-nitroimidazol-1-yl)acetate[1] (100 mg, 0.5 mmol) and the mixture stirred at room temperature for 5 minutes. The volatile components were then removed in vacuo to give a pale yellow solid which was shown to be N-(2-aminoethyl)-(2-nitroimidazol-1 -yl)acetamide in essentially quantitative yield.

$\delta_H$(D2O; 270 MHz) 2.56(2H, t, J=6 Hz), 3.03(2H, s), 3.13(2H, t, J=6 Hz), 5.03(2H, s), 7.05(1H, d, J=1 Hz), 7.26(1H, d, J=1 Hz).

$\delta_C$(D2O) 39.8(t), 41.8(t), 52.0(t), 128.0(d), 129.0(d), 144.5(s), 168.7(s).

N-{2-[(2-mercaptoethylthio)acetylamino]ethyl}-(2-nitroimidazol-1-yl)acetamide

N-(2-Aminoethyl)-(2-nitroimidazol-1-yl)acetamide (40 mg, 0.23 mmol) in methanol (0.5 cm$^3$) was added to 2-oxo-1,4-dithiane (40 mg, 0.27 mmol) in acetone (0.2 cm$^3$) under an atmosphere of dry nitrogen. The mixture was left at room temperature and monitored by n.m.r. spectroscopy until the reaction was complete. The bulk of the solvent was removed, and the resulting material purified by reverse phase h.p.l.c. using aqueous methanol as the eluant. The pure N-(2-[(2-mercaptoethylthio)acetylamino]ethyl)-(2-nitroimidazol -1-yl)acetamide (30 mg) was isolated as a pale yellow solid.

$\delta_H$(d$_6$-DMSO; 270 MHz) 2.62–2.79(4H, m), 3.10(2H, s), 3.13(4H, m), 5.05(2H, s), 7.17(1H, d, J=1 Hz), 7.57(1H, d, J=1 Hz), 8.06(1H, br s), 8.37(1H, br s).

$\delta_C$(d$_6$-DMSO) 23.9(t), 34.4(t), 35.8(t), 38.6(x2)(t), 51.7 (t), 127.6(d), 128.9(d), 145.0(s), 165.9(s), 169.5(s).

1. J. Parrick et al, *Synthesis,* 1991, 709

Preparation of N-[2-(N'-carbamoylmethyl)aminoethyl]-tetrahydropyran-2-ylthioacetamide [HL 33P]

N-(2-Aminoethyl)-tetrahydropyran-2-ylthioacetamide 1,2-Diaminoethane (21 g, 350 mmol) was added to methyl tetrahydropyran-2-ylthioacetate (20 g, 105 mmol) and the mixture heated at 75° C. for 2 h. Volatile components were then removed from the reaction mixture in vacuo to give the N-(2-aminoethyl)-tetrahydropyran-2-ylthioacetamide in essentially quantitative yield. This product was contaminated with a small quantity of 1,2-diaminoethane, but it was sufficiently pure to be used without further purification.

$\delta_H$(CDCl$_3$; 270 MHz) 1.43–1.92(6H, broad envelope of overlapping resonances), 2.75(2H, t, J=6 Hz), 3.21(1H, d, J=16 Hz), 3.24(2H, m), 3.25(1H, d, J=16 Hz), 3.45(1H, m), 3.95(1H, m), 4.73(1H, m), 7.31(1H, br s).

$\delta_C$(CDCl$_3$) 21.9(t), 25.1(t), 31.1(t), 34.8(t), 41.1(t), 42.4 (t), 65.8(t), 83.4(d), 169.6(s)

N-[2-(N'-Carbamoylmethyl)aminoethyl]-tetrahydropyran-2-ylthioacetamide

Chloroacetamide (0.48 g, 5.1 mmol) was added to a solution of N-(2-aminoethyl)-tetrahydropyran-2-ylthioacetamide (1 g, 5.1 mmol) in methanol (4 cm$^3$) and the mixture heated at 50° C. The progress of the reaction was followed by $^{13}$C n.m.r. When the ratio of starting material to product was 1:1, the heating was stopped and the volatile components removed in vacuo. The product was isolated from the residue by reverse phase h.p.l.c. using aqueous methanol as the eluant. The semi-solid product obtained in this way was triturated with diethyl ether and then dried in vacuo to give N-[2-(N'-carbamoylmethyl)aminoethyl]-tetrahydropyran- 2-ylthioacetamide (0.22 g) as a white solid.

$\delta_H$(CDCl$_3$; 270 MHz) 1.51–1.99(6H, broad envelope of overlapping resonances), 2.79(2H, t, J=6 Hz), 3.26(1H, t, J=16 Hz), 3.30(2H, s), 3.40(2H, m), 3.41(2H, t, J=16 Hz), 3.53(1H, m), 4.02(1H, m), 4.82(1H, m), 6.47(1H, br s), 7.25(1H, br s), 7.51(1H, br t, J=6 Hz).

$\delta_C$(CDCl$_3$) 22.0(t), 25.3(t), 31.2(t), 34.9(t), 39.3(t), 49.0 (t), 51.9(t), 65.9(t), 83.6(d), 170.2(s), 174.8(s).

Preparation of N-{2-[2-(N'-acetylamino)ethylthio]ethyl}-tetrahydropyran-2-ylt hioacetamide [HL 34P]

S-{N-[2-(N'-Acetylamino)ethyl] carbamoylmethyl}thioacetate

Acetic anhydride (10.8 g, 100 mmol) was added quickly to a stirred solution of 2-aminoethylthiol hydrochloride (4.6 g, 40 mmol) in water (20 cm$^3$) containing potassium hydroxide (4.5 g, 80 mmol). The mixture was stirred at room temperature for 2 h and then its acidity adjusted to pH 4 using hydrochloric acid. The water was then removed under reduced pressure to give a slurry which was extracted with acetone. Volatile components were then removed from the acetone extracts under reduced pressure to give the crude S-{N-[2-(N'-acetylamino)ethyl]carbamoylmethyl} thioacetate as a colourless liquid (5.5 g, ca. 85%). This material was used without further purification.

$\delta_C$(MeOH) 21.7(q), 28.3(t), 29.6(q), 39.1(t), 172.1(s), 195.6(s).

N-{2-[2-(N'-Acetylamino)ethylthio]ethyl}-tetrahydropyran-2-ylthioacetamide

N-(2-Chloroethyl)-tetrahydropyran-2-ylthioacetamide (0.45 g, 2 mmol), S-{N-[2-(N'-acetylamino)ethyl] carbamoylmethyl} thioacetate (0.65 g, 2 mmol), potassium hydroxide (0.6 g, 10 mmol), methanol (5 cm$^3$) and water (1 cm$^3$) were heated at 75° C. for 1 h. The methanol was removed under reduced pressure and the residue partitioned between chloroform (50 cm$^3$) and water (25 cm$^3$). The organic layer was separated, dried (MgSO$_4$), filtered, and the volatile components removed in vacuo to give the crude product. This material was purified, firstly by chromatography on silica using a mixture of ethyl acetate and methanol (96:4) as the eluant and then by reverse phase h.p.l.c. using aqueous methanol as the eluant. The pure N-{2-[2-(N'-acetylamino)ethylthio]ethyl}-tetrahydropyran-2-ylt hioacetamide (100 mg) was obtained as a colourless oil.

$\delta_H$(CDCl$_3$; 270 MHz) 1.44–1.93(6H, broad envelope of overlapping resonances), 1.92(3H, s), 2.60(2H, t, J=6.5 Hz), 2.62(2H, t, J=6.5 Hz), 3.18(1H, d, J=16 Hz), 3.34(1H, d, J=16 Hz), 3.39(2H, q, J=6.5 Hz), 3.43(2H, t, J=6.5 Hz), 3.45(1H, m), 3.96(1H, m), 4.75(1H, m), 6.58(1H, br t), 7.37(1H, br t).

$\delta_C$(CDCl$_3$) 21.8(t), 23.0(q), 25.1(t), 31.0(t), 31.5(×2)(t), 34.6(t), 38.6(t), 38.8(t), 65.6(t), 83.2(d), 169.8(s), 170.4(s).

Preparation of N{2-[N'-ethyl-N'-(N"-ethyl) carbamoylmethyl]aminoethyl}-tetrahy dropyran-2-ylthioacetamide [HL 46]

N-Ethyl-chloroacetamide (0.25 g, 2 mmol) was added to a solution of N-[2-(N'-ethylamino)ethyl]-tetrahydropyran-2-ylthioacetamide (0.5 g, 2 mmol) and triethylamine (0.2 g, 2 mmol) in tetrahydrofuran (5 cm$^3$) and the mixture heated at 60° C., and monitored by n.m.r. spectroscopy, until the reaction was complete (ca. 36 h). The volatile components were removed in vacuo and the product isolated by reverse phase h.p.l.c. using aqueous methanol as the eluant. N{2-[N'-Ethyl-N'-(N''-ethyl)carbamoylmethyl]aminoethyl}-tetrahydropyran-2-ylthioacetamide (0.28 g, 42%) was obtained as a colourless oil.

$\delta_H$(CDCl$_3$; 270 MHz) 0.94(3H, t, J=7 Hz), 1.06(3H, t, J=7 Hz), 1.42–1.89(6H, broad envelope of overlapping resonances), 2.50(2H, q, J=7 Hz), 2.53(2H, t, J=6 Hz), 2.99(2H, s), 3.17(1H, d, J=16.5 Hz), 3.16–3.27(4H, m), 3.32(1H, d, J=16.5 Hz), 3.43(1H, m), 3.92(1H, m), 4.68(1H, dd, J=7 and 3 Hz), 7.23–7.29(2H, br s).

$\delta_C$(CDCl$_3$) 11.5(q), 14.8(q), 21.9(t), 25.0(t), 31.1(t), 33.7(t), 34.8(t), 37.6(t), 48.9(t), 53.6(t), 58.1(t), 66.0(t), 83.6(d), 169.5(s), 174.1(s).

Preparation of N-[N'-(N''-Ethoxycarbonyl-2-aminoethyl)-N'-ethyl-2-aminoethyl]-tetrahydropyran-2-ylthioacetamide [HL 47].

N-Ethoxycarbonylaziridine[1] (0.24 g, 2 mmol) was added to a solution of N-[2-(N'-ethylamino)ethyl]-tetrahydropyran-2-ylthioacetamide (0.5 g, 2 mmol) in ethanol (2 cm$^3$) and the mixture stirred at room temperature. After 7 days the reaction was essentially complete. The solvent was removed under reduced pressure and the product isolated from the residue by reverse phase h.p.l.c. using aqueous methanol as the eluant. The pure N-[N'-(N''-ethoxycarbonyl-2-aminoethyl)-N'-ethyl-2-aminoethyl]-tetrahydropyran-2-ylthioacetamide (0.37 g, 51%) was isolated as a colourless oil. Found: C, 53.11; H, 8.92; N, 11.83. C$_{16}$H$_{31}$N$_3$O$_4$S requires C, 53.16; H, 8.64; N, 11.62%

$\delta_H$(CDCl$_3$; 270 MHz) 1.01 (3H, t, J=7 Hz), 1.25(3H, t, J=7 Hz), 1.46–1.98(6H, broad envelope of overlapping resonances), 2.52–2.61(6H, m), 3.22(2H, br m) 3.26(1H, d, J=16 Hz), 3.31(2H, m), 3.44(1H, d, J=16 Hz), 3.55(1H, m), 4.04(1H, m), 4.12(2H, q, J=7 Hz), 4.82(1H, m), 5.44(1H, br s), 7.39(1H, br s).

$\delta_C$(CDCl$_3$) 11.4(q), 14.7(q), 22.0(t), 25.2(t), 31.1(t), 34.7(t), 37.3(t), 38.8(t), 47.1(t), 52.1(t), 52.9(t), 60.7(t), 65.8(t), 83.4(d), 156.9(s), 169.4(s).

1. Y. Iwakura and A. Nabeya, *J. Org. Chem.,* 1960, 25, 1118.

Preparation of N-(2-Aminoethyl)-3-[2-(tetrahydropyran-2-ylthio)ethylthio]-propionamide [HL 48]

N-(2-Aminoethyl)-3-mercaptopropionamide

Methyl 3-mercaptopropionate (12.2 g, 10 mmol) was added to 1,2-diaminoethane (20 g, 33 mmol) and the mixture heated at 75° C. for 2 h. The excess of 1,2-diaminoethane was then removed in vacuo to give a colourless oil which was shown by n.m.r spectroscopy to be largely N-(2-aminoethyl)-3-mercaptopropionamide. This material was used without further purification.

$\delta_C$(CDCl$_3$) 19.8(t), 39.1(t), 40.5(t), 41.5(t), 170.7(q).

N-(2-Aminoethyl)-3-[2-(tetrahydropyran-2-ylthio)ethylthio]propionamide

N-(2-Aminoethyl)-3-mercaptopropionamide (6 g, 40 mmol) 2-(2-chloroethylthio)-tetrahydropyran (5 g, 27 mmol), potassium hydroxide (2.5 g, 44 mmol), and methanol (25 cm$^3$) were mixed together and heated at 75° C. for 35 min. The mixture was then filtered and volatile components removed from the filtrate under reduced pressure to leave a viscous residue. This material was purified firstly by chromatography on silica using a mixture of ethyl acetate, methanol and aqueous ammonia (83:15:5) as the eluant and then by reverse phase h.p.l.c. using aqueous methanol as the eluant. The pure N-(2-aminoethyl)-3-[2-(tetrahydropyran-2-ylthio)ethylthio]prop ionamide was obtained as a colourless viscous oil (1.5 g, 20%). Found: C, 48.45; H, 8.59; N, 9.47. C$_{12}$H$_{24}$N$_2$O$_2$S$_2$ requires C, 49.28; H, 8.27; N, 9.58%.

$\delta_H$(CDCl$_3$; 270 MHz) 1.52–1.98(6H, broad envelope of overlapping resonances), 1.89(3H, s), 2.49(2H, t, J=7 Hz), 2.73–2.89(6H, m), 3.30(2H, q, J=6 Hz), 3.52(1H, m), 4.05 (1H, m), 4.90(1H, m), 7.11(1H, br t, J=5 Hz).

$\delta_C$(CDCl$_3$) 21.2(t), 25.1(t), 27.4(t), 30.1(t), 30.9(t), 32.2 (t), 36.2(t), 41.0(t), 41.9(t), 64.2(t), 82.1(d), 171.2(s).

Preparation of N-(2-Acetylaminoethyl)-3-[2-(tetrahydropyran-2-ylthio)ethylthio[-propionamide [HL 49]

S-{2-[N-(2-Acetylaminoethyl)carbamoyl]ethyl} thioacetate

N-(2-Aminoethyl)-3-mercaptopropionamide (4.5 g, 30 mmol) was added to a solution of potassium hydroxide (1.68 g, 30 mmol) in water (25 cm$^3$). Acetic anhydride (4.08 g, 40 mmol) was then added dropwise and the mixture allowed to stand for 2 h. The acidity of the. solution was then adjusted to pH 4 using hydrochloric acid and the solvent was then removed under reduced pressure to give a white waxy solid. The solid was washed with ether and then dried to give the S-{2-[N-(2-acetylaminoethyl)carbamoyl]ethyl} thioacetate, together with inorganic salts, as a white solid.

$\delta_C$(H$_2$O) 23.3(q), 26.2(q), 31.4(t), 36.5(t), 39.8(t), 40.0(t), 175.4(s), 175.5(s) 201.9(s).

N-(2-Acetylaminoethyl)-3-[2-(tetrahydropyran-2-ylthio) ethylthio]propionamide

A quantity of the S-{2-[N-(2-acetylaminoethyl) carbamoyl]ethyl} thioacetate, prepared above, (3.2 g, 23 mmol), 2-(2-chloroethylthio)tetrahydropyran (2 g, 11 mmol), potassium hydroxide (2.5 g, 44 mmol), methanol (10 cm$^3$) and water (5 cm$^3$) were mixed together and heated at 75° C. for 30 min. The mixture was allowed to cool and then partitioned between chloroform (50 cm$^3$) and water (50 cm$^3$). The organic layer was separated and the aqueous layer extracted with a further portion of chloroform. The combined chloroform extracts were then dried (MgSO$_4$) and volatile components removed under reduced pressure to leave the crude product as an oily solid. A quantity of this material was purified firstly by chromatography on silica using a mixture of ethyl acetate, and methanol (95:5) as the eluant and then by reverse phase h.p.l.c. using aqueous methanol as the eluant. The pure N-(2-acetylaminoethyl)-3-[2-(tetrahydropyran-2-ylthio)ethylthi o]propionamide was obtained as a white solid (0.3 g).

Found: C, 49.34; H, 7.50; N, 7.84. C$_{14}$H$_{26}$N$_2$O$_3$S, requires C, 50.27; H, 7.83; N, 8.37%.

$\delta_H$(CDCl$_3$; 270 MHz) 1.47–1.96(6H, broad envelope of overlapping resonances), 1.91 (3H, s), 2.41(2H, t, J=7 Hz), 2.63–2.86(6H, m), 3.29(4H, m), 3.43(1H, m), 3.98(1H, m), 4.82(1H, m), 6.86(1H, br s), 7.07(1H, br s).

$\delta_C$(CDCl$_3$) 21.5(t), 23.1(q), 25.4(t), 27.6(t), 30.5(t), 31.2 (t), 32.5(t), 36.3(t), 39.6(t), 39.6(t), 64.5(t), 82.5(d), 171.5 (s), 172.3(s).

Preparation of N-(2-Aminoethyl)-3-[(2-acetylamino ethylthio]propionamide HL50

N-(2-Aminoethyl)-3-mercaptopropionamide (1.8 g, 12 mmol), N-(2-chloroethyl)-acetamide (1.8 g, 10 mmol), potassium hydroxide (1.0 g, 17 mmol) and methanol (15 cm$^3$) were heated under reflux for 1 h. After cooling, the mixture was filtered and organic solvent removed from the filtrate in vacuo to give a viscous yellow oil. A quantity of this material was purified firstly by chromatography on silica using a mixture of ethyl acetate, methanol and aqueous ammonia (45:45:10) as the eluant and then by reverse phase h.p.l.c. using aqueous methanol as the eluant. The pure N-(2-aminoethyl)-3-[(2-acetylamino)ethylthio]propionamide (400 mg) was obtained as a viscous oil.

$\delta_H$(D$_2$O; 270 MHz) 2.00(3H, s), 2.60(2H, t, J=7 Hz), 2.72(2H, t, J=7 Hz), 2.84(2H, t, J=7 Hz), 3.13(2H, t, J=6 Hz), 3.39(2H, t, J=7 Hz), 3.51 (2H, t, J=6 Hz).

δhd C(D$_2$O) 22.0(q), 26.8(t), 30.5(t), 35.6(t), 37.3(t), 38.7(t), 39.3(t), 174.1(s), 175.3(s).

Preparation of N-(2-Acetylaminoethyl)-[2-methyl-2-(tetrahydropyran-2-ylthio)propyl]thioacetamide [HL 52]

2-(2-Chloro-1,1-dimethyl-ethylthio)tetrahydropyran and 2-(2-methyl-2-chloroprorylthio)tetrahydropyran.

Hydrogen chloride gas was passed into a stirred solution of iso-butylenesulphide (1 g, 11.34 mmol) in diethylether (10 cm$^3$) at 0° C. until the solution was saturated. This mixture was stirred for 2h at 0° C. and 3,4-dihydropyran (0.95 g, 11.34 mmol) was then added dropwise. The reaction mixture was stirred for a further 2 h and the solvent then removed in vacuo to yield the crude product as a yellow viscous oil. This material was distilled in a short path distillation apparatus (at 0.01 mmHg) to give the product as a colourless oil (1 g, 42%), which was shown by n.m.r. spectroscopy to be a mixture of 2-(2-chloro-1,1-dimethyl-ethylthio)tetrahydropyran (55%) and 2-(2-methyl-2-chloropropylthio)tetrahydropyran (45%).

δ$_C$(CDCl$_3$); 21.2(t), 22.0(t), 25.3(q), 25.3(t), 25.5(t), 26.3 (t), 31.1 (t), 31.2(q), 31.4(t), 31.6(q), 45.2(t), 46.7(s ), 54.9(t), 64.1(t), 64.7(t), 69.0(s), 80.0(d), 82.9(d).

N-(2-Acetylaminoethyl)-[2-methyl-2-(tetrahydropyran-2-ylthio)propyl]thioacetamide To a quantity (0.8 g, 3.9 mmol) of the mixture of 2-(2-chloro-1,1-dimethyl-ethylthio)tetrahydropyran and 2-(2-methyl-2-chloropropylthio)tetrahydropyran, previously prepared, was added S-[N-(2-acetylaminoethyl) carbamoylmethyl] thioacetate (1.05 g, 5 mmol), potassium hydroxide (0.73 g, 12 mmol), methanol (8 cm$^3$) and water (2 cm$^3$). This mixture was stirred and heated at 75° C. for 20 min and then was allowed to cool. Volatile components were then removed under reduced pressure to leave the crude product as an oily solid which was partitioned between dichloromethane (25 cm$^3$) and water (25 cm$^3$). The organic layer was separated and the aqueous layer extracted with a further portion of dichloromethane (25 cm$^3$). The combined dichloromethane extracts were then dried (MgSO$_4$), filtered, and volatile components removed under reduced pressure to leave the crude product as an oily solid. This material was purified by reverse phase h.p.l.c. using aqueous methanol as the eluant. The pure N-(2-acetylaminoethyl)-[2-methyl-2-(tetrahydropyran-2-ylthio)propyl]thioacetamide was obtained as a white waxy solid (0.3 g, 45%). Found: C, 51.47; H, 8.20; N, 7.85. C$_{15}$H$_{28}$N$_2$O$_3$S$_2$ requires C, 51.69; H, 8.10; N, 8.04%.

δ$_H$(CDCl$_3$; 270 MHz) 1.40(3H, s), 1.45(3H, s) 1.51–1.93 (6H, broad envelope of overlapping resonances), 2.00(3H, s), 2.91(2H, t), 3.25(1H, d, J=16 Hz), 3.30(1H, d, J=16 Hz), 3.40(4H, m), 3.46(1H, m), 4.05(1H, m), 5,02(1H, m), 6.97 (1H, br s) 7.59(1H, br s).

δ$_C$(CDCl$_3$) 21.9(t), 22.9(q), 25.2(t), 28.1 (×2) (q), 28.1(t), 31.6(t), 37.4(t), 39.6(t), 39.6(t), 46.82(t), 47.0(t), 64.7(t), 80.1(d), 170.1 (q), 171.0(q).

Preparation of N-(2-{N',N'-Bis]2-(ethoxycarbonylamino) ethyl]}aminoethyl)-tetrahydropyran-2-ylthioacetamide [HL 53]

N.B. The conditions below were chosen to produce the monoalkylated system. The dialkylated system was produced as a side product—hence low yield N-Ethoxycarbonylaziridine (0.52 g, 4.5 mmol) was added to a solution of N-(2-aminoethyl)-tetrahydropyran-2-ylthioacetamide (1 g, 4.5 mmol) in ethanol (10 cm$^3$) and the mixture stirred at room temperature for 2 days. The solvent was removed under reduced pressure to give a residue which was shown to contain the monoalkylated and some of the dialkylated amine. A sample of this latter product was isolated from the residue by reverse phase h.p.l.c. using aqueous methanol as the eluant. The N-(2-{N',N'-bis[2-(ethoxycarbonylamino)ethyl]}aminoethyl)-tetrahydropyran-2-ylthioacetamide (0.13 g, 13%) was isolated as a colourless oil.

δ$_H$(CDCl$_3$; 270 MHz) 1.24(6H, t, J=7 Hz), 1.50–2.05(6H, broad envelope of overlapping resonances), 2.57(6H, m), 3.13–3.42(6H, broad envelope of overlapping resonances), 3.28(1H, d, J=16 Hz), 3.44(1H, d, J=16 Hz), 3.54(1H, m), 4.05(1H,m)a, 4.11(4H, q, J=7 Hz), 4.83(1H, m), 5.45(2H, br s), 7.38(1H, br s).

δ$_C$(CDCl$_3$) 14.7(×2) (q), 22.0(t), 25.2(t), 31.1(t), 34.4(t), 37.6(t), 38.9(t), 53.4(t), 53.9(t), 60.8(×2)(t), 65.8(t), 83.3(d), 157.1(s), 170.1(s).

Preparation of N-(2-Acetylaminoethyl)-3-(tetrahydropyran-2-ylthio)propylthio-acetamide [HL 58]

Methyl (3-mercaptopropyl thioacetate

Methyl chloroacetate (1.95 g, 18 mmol) was added to a solution of propane-1,3-dithiol (6.42 g, 59 mmol) and potassium hydroxide (1.11 g, 20 mmol) in methanol (30 cm$^3$), and the mixture was heated at 75° C. for 30 min. After cooling the mixture was filtered and the filtrate evaporated to dryness under reduced pressure (65° C. at 0.05 mmHg) to give the methyl (3-mercaptopropyl)thioacetate (2.27 g, 70%). This material was sufficiently pure to be used without further purification.

δ$_H$(CDCl$_3$; 270 MHz) 1.39(1H, t, J=8 Hz), 1.91(2H, p, J=8 Hz), 2.65(2H, q, J=8 Hz), 2.78(2H, t, J=8 Hz), 3.22(2H, s), 3.75(3H, s).

δ$_C$(CDCl$_3$) 23.2(t), 30.9(t), 32.6(t), 33.3(t), 52.4(q), 170.9 (s).

Methyl [3-(tetrahydropyran-2-ylthio)propyl]thioacetate

Dihydropyran (1.58 g, 19 mmol) in diethyl ether (15 cm$^3$) was added to a solution of methyl (3-mercaptopropyl) thioacetate (2.27 g, 13 mmol) in diethyl ether (10 cm$^3$). Hydrogen chloride gas was passed into this mixture until it began to feel warm, and the mixture was then allowed to stand at room temperature overnight in a closed vessel. Volatile components were then removed under reduced pressure (45° C. at 20 mmHg) to give the methyl {3-[2-(tetrahydropyranyl)thio]propyl}thioacetate (3.14 g,94%) as a colourless oil. This material was sufficiently pure to be used without further purification.

δ$_C$(CDCl$_3$) 21.7(t), 25.6(t), 29.1(t), 29.1(t), 31.4(t), 31.5 (t), 33.3(t), 52.4(q), 64.5(t), 82.3(d), 170.8(s).

N-(2-Acetylaminoethyl)-3-(tetrahydropyran-2-ylthio) propylthioacetamide

Methyl [3-(tetrahydropyran-2-ylthio)propyl]thioacetate (1 g, 3.7 mmol) was added dropwise to N-(2-aminoethyl)-acetamide (1.25 g, 12.25 mmol) and the mixture heated at 75° C. for 2.5 h. Volatile components were then removed under reduced pressure (45° C. at 0.02 mmHg) to give an oil which was taken up into water. This aqueous solution was then extracted with dichloromethane (adding potassium chloride to the aqueous layer to prevent emulsion formation if necessary). The dichloromethane extracts were then dried (MgSO$_4$), filtered, and the solvent removed under reduced pressure to give the crude N-(2-acetylaminoethyl)-3-(tetrahydropyran-2-ylthio)propylthioa cetamide. A pure sample of this material (0.25 g, 22%) was obtained by reverse phase h.p.l.c. using aqueous methanol as the eluant.

δ$_H$(CDCl$_3$; 270 MHz) 1.57–1.99(6H, broad envelope of overlapping resonances), 1.91(2H, p, J=7 Hz), 1.99(3H, s), 2.66(2H, t, J=7 Hz), 2.63–2.81 (2H, m), 3.21 (2H, s), 3.43(4H, br m) 3.49(1H, m), 4.06(1H, m), 4.82(1H, m), 6.45(1H, br s) 7.38(1H, br s).

δ$_C$(CDCl$_3$) 21.8(t), 23.1(q), 25.5(t), 29.1(t), 29.2(t), 31.4 (t), 31.6(t), 35.7(t), 39.6(t), 39.8(t), 64.9(t), 82.5(d), 170.4 (s), 171.4(s).

Preparation of N-(2-Aminoethyl)-3-(tetrahydropyran-2-ylthio)propylthioacetamide [HL 59]

Methyl [3-(tetrahydropyran-2-ylthio)propyl]thioacetate (1 g, 3.7 mmol) was added dropwise to 1,2-diaminoethane (0.75 g, 12.5 mmol) and the mixture heated at 75° C. for 6 h. Volatile components were then removed under reduced pressure (65° C. at 0.1 mmHg) to give the crude N-(2-aminoethyl)-3-(tetrahydropyran-2-ylthio)-propylthioacetamide as a colourless oil. A pure sample of this material (0.23 g, 21%) was obtained by reverse phase h.p.l.c. using aqueous methanol as the eluant.

$\delta_H$(CDCl$_3$; 270 MHz) 1.48–1.97(6H, broad envelope of overlapping resonances), 1.92(2H, p, J=7 Hz), 2.68(2H, t, J=6 Hz), 2.62–2.82(2H, m), 2.86(2H, t, J=6 Hz), 3.24(2H, s), 3.34(2H, q, J=6Hz), 3.51(1H, m), 4.06(1H, m), 4.83(1H, m), 7.30(1H, br s).

$\delta_C$(CDCl$_3$) 21.8(t), 25.6(t), 29.1(t), 29.2(t), 31.4(t), 31.8 (t), 36.1(t), 41.4(t), 42.4(t), 64.7(t), 82.5(d), 169.1(s)

Preparation of N-(3-Acetylamino)propyl-2-(tetrahydropyran-2-ylthio)ethylthio-acetamide HL60

S-[N-(3-Acetylaminopropyl)carbamoylmethyl]thioacetate

Methyl mercaptoacetate (7.5 g, 70 mmol) was added quickly to 1,3-diaminopropane (20 g, 270 mmol). Following an initial rise in temperature the reaction mixture was maintained at 70° C. for 2.5 h, and the 1,3-diaminopropane then removed under reduced pressure. This crude N-(3-aminopropyl)-mercaptoacetamide was dissolved in water (70 cm$^3$) and acetic anhydride (20 g, 100 mmol) added. After an initial rise in temperature the reaction mixture was left to stir overnight at room temperature. The volatile components were then removed in vacuo to give a dark viscous residue which was shown by n.m.r. spectroscopy to contain the required product. Pure S-[N-(3-acetylaminopropyl)carbamoylmethyl]thioacetate (5.0 g, 31%) was obtained as a light brown solid by chromatography on silica using a mixture of ethyl acetate and methanol (90:10) as the eluant.

$\delta_H$(CDCl$_3$; 270 MHz) 1.64(2H, p, J=6 Hz), 2.00(3H, s), 2.41(3H, s), 3.25(2H, m), 3.60(2H, s), 7.18(1H, br t, J=6 Hz), 7.49(1H, br t, J=6 Hz).

$\delta_C$(CDCl$_3$) 20.7(t), 28.9(t), 29.9(t), 32.8(t), 35.8(t), 36.3 (t), 168.3(s), 171.0(s), 194.8(s).

N-(3-acetylamino)propyl-2-(tetrahydropyran-2-ylthio)ethylthioacetamide

S-[N-(3-Acetylaminopropyl)carbamoylmethyl]thioacetate (2.9 g, 12.5 mmol) 2-(2-chloroethylthio)tetrahydropyran (1.60 g, 8.9 mmol), potassium hydroxide (1.68 g, 30 mmol), methanol (8 cm$^3$) and water (2 cm$^3$) were mixed together and heated at 75° C. for 45 min. The mixture was then filtered and volatile components removed from the filtrate under reduced pressure to leave a viscous residue. This material was then dissolved in dichloromethane (50 cm$^3$) and extracted with water (2×30 cm$^3$). The dichloromethane solution was then dried (MgSO$_4$), filtered,and volatile components removed from the filtrate under reduced pressure to give the desired ligand (700 mg) in a good state of purity. Final purification was achieved by reverse phase h.p.l.c. using aqueous methanol as the eluant. The pure N-(3-acetylamino)propyl-2-(tetrahydropyran-2-ylthio)ethylthioa cetamide was obtained as a colourless viscous oil.

Found: C, 49.10; H, 8.85; N, 8.09. C$_{14}$H$_{26}$N$_2$O$_3$S$_2$ requires C, 50.27; H, 7.83; N, 8.37%.

$\delta_H$(CDCl$_3$; 270 MHz) 1.52–1.98(6H, broad envelope of overlapping resonances), 1.68(2H, p, J=6 Hz), 2.00 (3H, s), 2.76–2.91 (4H, m), 3.26 (2H, s), 3.20–3.34(4H, m), 3.50 (1H, m), 4.04(1H, m), 4.90(1H, m), 7.19(1H, br t, J=6 Hz), 7.69(1H, br t, J=6 Hz).

$\delta_C$(CDCl$_3$) 21.2(t), 22.7(q), 25.1(t), 29.1(t), 29.7(t), 30.9 (t), 32.9(t), 35.4(t), 35.8(t), 36.2(t), 64.1(t), 82.1(d), 169.5 (s), 170.7(s).

Preparation of N-[3-(N'-ethylcarbamoylmethylthio)propyl]-tetrahydropyran-2-ylthioacetamide [HL 61]

N-(3-Hydroxypropyl)-tetrahydropyran-2-ylthioacetamide

Methyl tetrahydropyran-2-ylthioacetate (9.7 g, 50 mmol) was heated with 3-aminopropanol (7.5 g, 100 mmol) for 2 h at 75° C. The product was then purified on silica by flash chrotatography, using a mixture of 20 ethylacetate and methanol (98:2) as the eluant, to give N-(3-hydroxypropyl)-(tetrahydropyran-2-ylthio)acetamide (5.8 g, 50%) as a viscous oil.

$\delta$H(CDCl$_3$; 270 MHz) 1.53–2.01(6H, broad envelope of overlapping resonances), 1.72(2H, p, J=6 Hz), 3.25(1H, d, J=16 Hz), 3.36–3.44(3H, m) 3.53(1H, m), 3.64(2H, t, J=6 Hz), 4.03(1H, m), 4.15(1h, br s), 4.84 (1H, m) 7.57(1H, br s).

$\delta_C$(CDCl$_3$) 21.3(t), 24.8(q), 30.6(t), 31.5(t), 33.9(t), 36.3 (t), 58.8(t), 64.9(t), 82.6(d), 170.1(s), N-(3-Chloropropyl)-tetrahydropyran-2-ylthioacetamide Thionyl chloride (3.5 g, 30 mmol) in chloroform (20 cm$^3$) was added dropwise to a solution of N-(3-hydroxypropyl)-(tetrahydropyran-2-ylthio)acetamide 35 (5.5 g, 23.5 mmol) and triethylamine (3.5 g, 35 mmol) in chloroform (50 cm$^3$), and the mixture stirred at room temperature for 48 h. The resulting solution was extracted with water (2×35 cm$^3$), dried (MgSO$_4$), filtered, and volatile components removed under reduced pressure to give the N-(3-chloropropyl)-tetrahydropyran-2-ylthioacetamide (1.5 g, 25%) as an oil. This material was sufficiently pure to be used without further purification.

$\delta_C$(CDCl$_3$) 22.0(t), 25.3(t), 31.2(t), 32.0(t), 34.8(t), 37.0 (t), 42.4(t), 65.9(t), 83.5(d), 170.1(q).

Methyl 3-(tetrahydropyran-2-ylthioacetylamino) propylthioacetate

A stirred mixture of N-(3-chloropropyl)-tetrahydropyran-2-ylthioacetamide (1.5 g, 6.8 mmol), methyl mercaptoacetate (1.1 g, 10 mmol), potassium hydroxide (0.58 g, 10 mmol), and methanol (10 cm$^3$) was heated at 75° C. for 30 min. The mixture was then allowed to cool, filtered, and the methanol then removed under reduced pressure. This residue was then partitioned between dichloromethane (30 cm$^3$) and water (30 cm$^3$). The organic phase was then separated, dried (MgSO$_4$), filtered, and the solvent removed under reduced pressure. The residue was purified by chromatography on alumina using ethyl acetate as the eluant to give the pure methyl 3-(tetrahydropyran-2-ylthioacetylamino) propylthioacetate as a viscous oil (0.66 g, 30%).

$\delta_C$(CDCl$_3$) 21.2(t), 24.6(t), 27.9(t), 29.1(t), 30.4(t), 32.5 (t), 33.9(t), 37.7(t), 51.6(t), 64.7(t), 82.4(d), 169.0(q), 170.1 (q).

N-[3-(N'-Ethylcarbamoylmethylthio)propyl]-tetrahydropyran-2-ylthioacetamide

A mixture of methyl 3-(tetrahydropyran-2-ylthioacetylamino)propylthioacetate (600 mg, 1.87 mmol), methanol (2 cm$^3$), and aqueous ethylamine (20 cm$^3$, 70%) was left to stand for 3 days. Volatile components were then removed from the filtrate under reduced pressure to leave a viscous residue. This material was purified by reverse phase h.p.l.c. using aqueous methanol as the eluant. The pure N-[3-(N'-ethylcarbamoylmethylthio)propyl]-tetrahydropyran-2-yl thioacetamide was obtained as a pale yellow viscous oil (450 mg, 71%). Found: C, 50.28; H, 8.57; N, 8.27. C$_{14}$H$_{26}$N$_2$O$_3$S$_2$ requires C, 50.27; H, 7.83; N, 8.37%.

$\delta_H$(CDCl$_3$; 270 MHz) 1.17(3H, t, J=7 Hz), 1.54–1.95(6H, broad envelope of overlapping resonances), 1.83(2H, p, J=7 Hz), 2.63(2H, t, J=7 Hz), 3.21(2H, s), 3.22–3.42(6H, broad envelope of overlapping resonances), 3.53(1H, m), 4.03(1H, m), 4.89(1H, m), 7.44(1H, br t, J=5 Hz), 7.59(1H, br t, J=5 Hz).

$\delta_C$(CDCl$_3$) 14.0(q), 21.1(t), 24.6(t), 28.1(t), 29.3(t), 30.4(t), 33.8(t), 33.9(t), 35.1(t), 37.7(t), 64.7(t), 82.4(d), 168.5(s), 169.3(s).

We claim:

1. Ligands of the formula

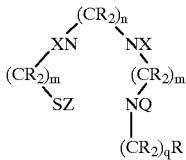

having an SNNN donor set, where
Z=H or a thiol protecting group,
m=2 or 3
n=2 or 3
q=1 or 1
R=same or different and is H, $C_1$–$C_{20}$ alkyl, alkenyl, alkoxy, alkoxyalkyl, $C_{1-20}$ primary, secondary or tertiary amide, $C_{1-20}$ primary, secondary or tertiary amine, $C_{1-20}$ carboxylic acid, $C_{1-20}$ hydroxyalkyl, $C_{1-20}$ aryl, or two Rs and any CR$_2$ group or two or more adjacent CR$_2$ groups are combined to form a $C_{3-6}$ cycloalkyl, aryl, heteroaryl, spiropiperidinyl or other saturated or unsaturated heterocyclic ring, or a CR$_2$ group adjacent —NR— represents CO and form together with —NR— a —CONR— amide group, or at least one R represents a targeting group or a protein reactive functionality,
X,Q=R
and pharmaceutically acceptable salts of the ligands, provided that
i) two of the X and Q groups are H, and the remaining X or Q group is not H;
ii) at least one CR$_2$ group represents CO and forms, together with an adjacent N atom, a —CONR— amide group,
iii) when each X is H, then neither Q nor (CR$_2$)$_q$R is H and only one or two CR$_2$ groups represents CO and forms, together with an adjacent N atom, a —CONR— group,
iv) when one or more R is $C_{1-5}$ carboxyl, then at least one CR$_2$ group that represents CO and forms, together with an adjacent N atom, a —CONR— amide group, is selected from (CR$_2$)$_m$ and (CR$_2$)$_q$.

2. Ligands as claimed in claim 1, wherein two CR$_2$ groups represent CO and form, together with adjacent nitrogen atoms, two —CONR— amide groups.

3. Ligands as claimed in claim 1, wherein at least one R represents a targeting group having a molecular weight below 1000 daltons.

4. Ligands a claimed in claim 1, wherein at least one R represents a targeting group which is a bioreductive group.

5. Radiometal complexes of the ligands claimed in claim 1.

6. Radiometal complexes as claimed in claim 5 which are electrically neutral.

7. Radiometal complexes as claimed in claim 5, which have human plasma protein binding of below 40%.

8. Radiometal complexes as claimed in claim 5, wherein the radiometal is selected from $^{99m}$Tc, $^{186}$Re, $^{188}$Re, $^{67}$Cu and $^{107}$Ag.

9. Radiometal complexes as claimed in claim 5, wherein the radiometal is $^{99m}$Tc and the complex has the formula

where L is the ligand of the formula

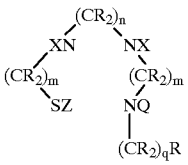

having an SNNN donor set, where
Z=H or a thiol protecting group,
m=2 or 3
n=2 or 3
q=0 or 1
R=same or different and is H, $C_1$–$C_{20}$ alkyl, alkenyl, alkoxy, alkoxyalkyl, $C_{1-20}$ primary, secondary or tertiary amide, $C_{1-20}$ primary, secondary or tertiary amine, $C_{1-20}$ carboxylic acid, $C_{1-20}$ hydroxyalkyl, $C_{1-20}$ aryl, or two Rs and any CR$_2$ group or two or more adjacent CR$_2$ groups are combined to form a $C_{3-6}$ cycloalkyl, aryl, heteroaryl, spiropiperidinyl or other saturated or unsaturated heterocyclic ring, or a CR$_2$ group adjacent —NR— represents CO and form together with —NR— a —CONR— amide group, or at least one R represents a targeting group or a protein reactive functionality,
X,Q=R
and pharmaceutically acceptable salts of the ligands, provided that
i) two of the X and Q groups are H, and the remaining X or Q group is not H;
ii) at least one CR$_2$ group represents CO and forms, together with an adjacent N atom, a —CONR— amide group,
iii) when each X is H, then neither Q nor (CR$_2$)$_q$R is H and only one or two CR$_2$ groups represents CO and forms, together with an adjacent N atom, a —CONR— group,
iv) when one or more R is $C_{1-5}$ carboxyl, then at least one CR$_2$ group that represents CO and forms, together with an adjacent N atom, a —CONR— amide group, is selected from (CR$_2$)$_m$ and (CR$_2$)$_q$.

* * * * *